United States Patent [19]

Traish

[11] Patent Number: 5,744,356
[45] Date of Patent: Apr. 28, 1998

[54] SPECIFIC ANTIBODIES AGAINST AN EPITOPE EXISTING WITHIN THE A/B REGION OF ESTROGEN RECEPTOR PROTEINS

[75] Inventor: Abdulmaged M. Traish, Belmont, Mass.

[73] Assignee: Trustees of Boston University, Boston, Mass.

[21] Appl. No.: 509,570

[22] Filed: Jul. 31, 1995

Related U.S. Application Data

[63] Continuation-in-part of Ser. No. 419,975, Apr. 7, 1995, abandoned, which is a continuation-in-part of Ser. No. 243,652, May 13, 1994, abandoned, which is a continuation-in-part of Ser. No. 784,626, Nov. 1, 1991, Pat. No. 5,312,752, which is a continuation of Ser. No. 388,091, Jul. 31, 1989, abandoned.

[51] Int. Cl.$^6$ .................................. C07K 16/28; C12N 5/12
[52] U.S. Cl. .......................... 435/334; 435/331; 435/332; 530/388.22; 530/387.9
[58] Field of Search .................... 435/240.27, 331, 435/332, 334; 530/388.2, 387.9

[56] References Cited

U.S. PATENT DOCUMENTS 5,312,752  5/1994  Wotiz .

*Primary Examiner*—Lila Feisee
*Assistant Examiner*—Nancy A. Johnson
*Attorney, Agent, or Firm*—David Prashker

[57] ABSTRACT

A unique monoclonal antibody is provided for determining the functional status of human estrogen receptor protein. The monoclonal antibody will specifically bind and react with an epitope present within the transactivation function, A/B domain of the human estrogen receptor protein. The functional status of the A/B domain is determined by identifying and discriminating among the 8S, 4S, 5S isoforms of the A/B region as these exist in the human estrogen receptor protein.

8 Claims, 19 Drawing Sheets

```
-128  GAGTTGTGCCTGGAGTGATGTTTAAGCCAATGTCAGGGCAAGGCAACAGTCCCTGGCCGTCCTCCA
                       +1
  -8  GGGAGCCCAGGAGCTGGCGGAGGGGCGTTCGTCCTGGGAGCTGCACTTGCTCCGTCGGGTCGCCGGC

113  CGGGACATGCGCGCTGCGTCGCCCTCTAACCTCGGGCTGTGCTCTTTTTCCAGGTGGCCGCCGGTTTC

233  ATG ACC ATG ACC CTC CAC ACC AAA GCA TCT GGG ATG GCC CTA CTG
      Met Thr Met Thr Leu His Thr Lys Ala Ser Gly Met Ala Leu Leu

323  CTC AAG ATC CCC GAG CTG CCC CGG GAG CTG CCC CTG TAC CTG GAC
      Leu Lys Ile Pro Glu Leu Pro Arg Glu Leu Pro Leu Tyr Leu Asp
                          SacII(b)
 413  GAG TTC AAC GCC GCG GCC GCC GGT TTC CCC AAC GCG CAG TAC CAG
      Glu Phe Asn Ala Ala Ala Ala Gly Phe Pro Asn Ala Gln Tyr Gln

503  TCC AAC GGC CTG CTG GGG CAC CAG CGA AAT CCC CTC TAC AGC GTG TCT CCG
      Ser Asn Gly Leu Leu Gly His Gln Arg Asn Pro Leu Tyr Ser Pro Pro

593  CTG CAG CCC GGC CAC GGC CAG GTG AAT CGA TAT TAC TAC CTG GAG AAC GAG
      Leu Gln Pro Gly His Gly Gln Val Asn Arg Tyr Tyr Tyr Leu Glu Asn Glu

683  AGG CCA AAT GAT TCA TGC GCA GTG CGA CAG GGT TAT GGC AGA GAA TTG
      Arg Pro Asn Asp Ser Ala Val Arg Gln Gly Gly Arg Glu Leu

773  GAG ACT CGC TAC TGT AAC GAC CAT GCT GAC TAT TCA GGC TAC
      Glu Thr Arg Tyr Cys Asn Asp His Ala Asp Tyr Ser Gly Tyr

863  AGA AGT ATT CAA CGA TAT CAT ATG TGT CCA GCC ACC AAC
      Arg Ser Ile Gln Arg Tyr His Met Cys Pro Ala Thr Asn

953  CGG CTC CGC AAA TAC GAA GTG GGA ATG ATG AAA GGT GCG ATA
      Arg Leu Arg Lys Tyr Glu Val Gly Met Met Lys Gly Ile

1043  AGA GAT GAT GGG GAG CGC AGG CGT GGG GAA GTG TCT GCT GGA GAC
      Arg Asp Asp Gly Glu Arg Arg Gly Glu Val Gly Ser Ala Gly Asp
```

FIG. 1B-1

```
GCACCTTTGTAATGCATATGAGCTCGGGAGACCAGTACTTAAAGTTGGACCCCC
                              Smal(a)
TTCACCGGACCGCAGGCTCCCGGGGCAGGGCCGGGGCCAGAGCTCGCGTCGG
                    Smal(b)                SacII(a)
TGAGCCTTCTGCCCTGCGGGGACACGGTCTGCACCCTGCCCGGCCACGGACC
```

| | | | | | | | | | | |
|---|---|---|---|---|---|---|---|---|---|---|
| CAT His | CAG Gln | ATC Ile | CAA Gln | GCG Gly | AAC Asn | GAG Glu | CTG Leu | CCC Pro | CTG Leu | ATC Asn | CGT Arc | CCG Pro | CAG Gln | 30 |
| AGC Ser | AGC Ser | AAG Lys | CCC Pro | GCC Ala | GTG Val | TAC Tyr | AAC Asn | TAC Tyr | CCC Pro | GAG Glu | GGC Gly | GCC Ala | GCC Ala | TAC Tyr | 60 |
| ACC Thr | GGC Gly | CTC Leu | CCC Pro | TAC Tyr | GGC Gly | TCT Ser | CCC Pro Smal(c) | GGG Gly | GAG Glu | GCT Ala PvuII | GCG Ala (b) | GCG Ala | TTC Phe | GGC Gly | 90 |
| AGC Ser | CCG Pro | CTG leu | ATG Met | CTA Leu | CTG Leu | CAC His | CCG Pro | CCG Pro | CCG Pro | CAG Gln | CTG Leu | TCG Ser | CCT Pro | TTC Phe | 120 |
| CCC Pro | AGC Ser | CGC Arg | TAC Tyr | ACG Thr | GTG Val | CGC Arg | GAG Glu | GCC Ala | GGC Gly | CCG Pro | CCG Pro | GCA Ala | TTC Phe | TAC Tyr | 150 |
| GCC Ala | AGT Ser | ACC Thr | AAT Asn | GAC Asp | AAG Lys | GGA Gly | AGT Ser | GAG Glu | ATG Met | GCT Ala | GAA Glu | TCT Ser | GCC Ala | AAG Lys | 180 |
| CAT His | TAT Tyr | GGA Gly | GTC Val | GGG Trp | TCC Ser | TGT Cys | GAG Glu | GGC Gly | TGC Cys | AAG Lys | GCC Ala | TTC Phe | TTC Phe | AAG Lys | 210 |
| CAG Gln | TGC Cys | ACC Thr | ATT Ile | GAT Asp | GCT Ala | AAA Lys | AAC Asn | AGG Arg | AGG Arg | AAG Lys | AGC Ser | TGC Cys | GCC Ala | TGC Cys | 240 |
| CGA Arc | AAA Lys | GAC Asp | CGA Arg | AGA Arg | GGA Gly | GGG Gly | AGA Are | ATG Met | TTG Leu | CAC His | AAA Lys | CAC His | CGC Arg | CAG Gln | 270 |
| ATG Met | AGA Arg | GCT Ala | GCC Ala | AAC Asn | CTT Leu | AGA Arg | AAC Asn | CCA Pro | AGC Ser | CCG Pro | CTC Leu | ATG Met | ATC Ile | AAA Lys | CGC Arg | 300 |

FIG. IB-2

| Pos | | | | | | | | | | | | | | |
|-----|---|---|---|---|---|---|---|---|---|---|---|---|---|---|
| 1133 | TCT Ser | AAG Lys | AAC Asn | AGC Ser | CTG Leu | GCC Ala | TTG Leu | TCC Ser | CTG Leu | ACC Thr | GCC Ala | GAC Asp | CAG Gln | ATG Met |
| 1223 | TAT Tyr | GAT Asp | ACC Thr | AGA Arg | CCC Pro | TTC Phe | AGT Ser | GAA Glu | GCT Ala | TCG Ser | ATG Met | ATG Met | GGC Gly | TTA Leu |
| 1313 | GCG Ala | AAG Lys | ACG Arg | GTG Val | CCA Pro | GGC Gly | TTT Phe | GAT Asp | TTG Leu | ACC Thr | CTC Leu | CAT His | GAT Asp | CAG Gln |
| 1403 | CTC Leu | GTC Val | TCG Trp | CGC Arg | TCC Ser | ATG Met | GAG Glu | CAC His | CCA Pro | AAG Lys | CTA Leu | CTG Leu | TTT Phe | GCT Ala |
| 1493 | ATG Met | CTG Leu | GAG Glu | ATC Ile | TTC Phe | GAC Asp | ATG Met | CTG Leu | CTG Leu | GCT Ala | TCA Ser | TCT Ser | CGG Arg | TTC Phe |
| 1583 | ATT Ile | ATT Ile | TTG Leu | CTT Leu | AAT Asn | TCT Ser | GGA Gly | GTG Val | TAC Tyr | ACA Thr | TTT Phe | TCC Ser | AGC Ser | ACC Thr |
| 1673 | AAG Lys | ATC Ile | ACA Thr | GAC Asp | ACT Thr | TTG Leu | ATC Ile | CAC His | CTG Leu | ATG Met | GCC Ala | AAG Lys | GCA Ala | GGC Gly | CTG Leu |
| 1763 | CTC Leu | TCC Ser | CAC His | ATC Ile | AGG Arg | ATG Met | AGT Ser | AAC Asn | AAA Lys | GGC Gly | ATG Met | GAG Glu | CAT His | CTG Leu |
| 1853 | CTG Leu | GAG Glu | ATG Met | CTG Leu | GAC Asp | GCC Ala | CAC His | CGC Arg | CTA Leu | CAT His | GCG Ala | CCC Pro | ACT Thr | AGC Ser | CGT Arg |
| 1943 | GCG Ala | GGC Gly | TCT Ser | ACT Thr | TCA Ser | TCG Ser | CAT His | TCC Ser | TTG Leu | CAA Gln | AAG Lys | TAT Tyr | TAC Tyr | ATC Ile | ACG Thr |

FIG. 1B-3

```
GTC  AGT  GCC  TTG  GAT  GCT  GAG  CCC  ATA  CTC  TAT  TCC  GAG  330
Val  Ser  Ala  Leu  Asp  Ala  Glu  Pro  Ile  Leu  Tyr  Ser  Glu

CTG  ACC  AAC  CTG  GCA  GAC  AGG  CAG  CTG  GTT  CAC  ATG  ATC  AAC  TGG  360
Leu  Thr  Asn  Leu  Ala  Asp  Arg  Gln  Leu  Val  His  Met  Ile  Asn  Trp

GTC  CTT  CTA  GAA  TGT  GCC  TGG  CTA  GAG  ATC  ATG  ATG  ATT  GGT  390
Val  Leu  Leu  Glu  Cys  Ala  Trp  Leu  Glu  Ile  Met  Met  Ile  Gly

CCT  AAC  TTG  CTC  TTG  GAC  AGG  AAC  CAG  GGA  AAA  TGT  GTA  GAG  GGC  420
Pro  Asn  Leu  Leu  Leu  Asp  Arg  Asn  Gln  Gly  Lys  Cys  Val  Glu  Gly

CGC  ATG  AAT  CTG  CAG  GAG  GAG  GGA  GAG  TTT  GTG  TGC  CTC  AAA  TCT  450
Arg  Met  Asn  Leu  Gln  Glu  Glu  Gly  Glu  Phe  Val  Cys  Leu  Lys  Ser

CTG  AAG  TCT  CTG  GAA  GAG  CAG  CAC  ATC  GCC  CAG  CGA  CTC  CTC  GAC  480
Leu  Lys  Ser  Leu  Glu  Glu  Gln  His  Ile  Ala  Gln  Arg  Leu  Leu  Asp

ACC  CTG  CAG  CAG  CAC  AAG  CGG  GTG  ACG  GAG  CAG  CTC  TAT  GAC  CTG  ATC  510
Thr  Leu  Gln  Gln  His  Lys  Arg  Val  Thr  Glu  Gln  Leu  Tyr  Asp  Leu  Ile

TAC  AGC  ATG  AAG  TGC  AAG  AAC  GTG  GTG  CCC  CTC  TAT  GAC  CTG  CTG  540
Tyr  Ser  Met  Lys  Cys  Lys  Asn  Val  Val  Pro  Leu  Tyr  Asp  Leu  Leu

GGA  GCA  TCC  GTG  GTG  GAG  ACG  GAG  CAA  AGC  CAC  TTG  GCC  ACT  570
Gly  Ala  Ser  Val  Val  Glu  Thr  Glu  Gln  Ser  His  Leu  Ala  Thr

GGG  GCA  GCA  GAG  GGT  TTC  CCT  GCC  ACA  GTC  TGA  GAG  CTC  CCT  CGC  595
Gly  Ala  Ala  Glu  Gly  Phe  Pro  Ala  Thr  Val  ***
```

*Full-length nucleotide sequence and deduced amino-acid sequence of the MCF-7 ER mRNA. The 5-flanking sequence of the human ER gene is shown from -128 to the cap site at nucleotide +1 (arrow). The ER mRNA sequence begins at nucleotide +1 and ends at the start of the poly(A) tail at nucleotide +6,322. The numbers on the left refer to the position of the nucleotides and those on the right to that of the amino acids.

* From: Green et al., Nature 320: 134-139 (1986)

FIG. 1B-4

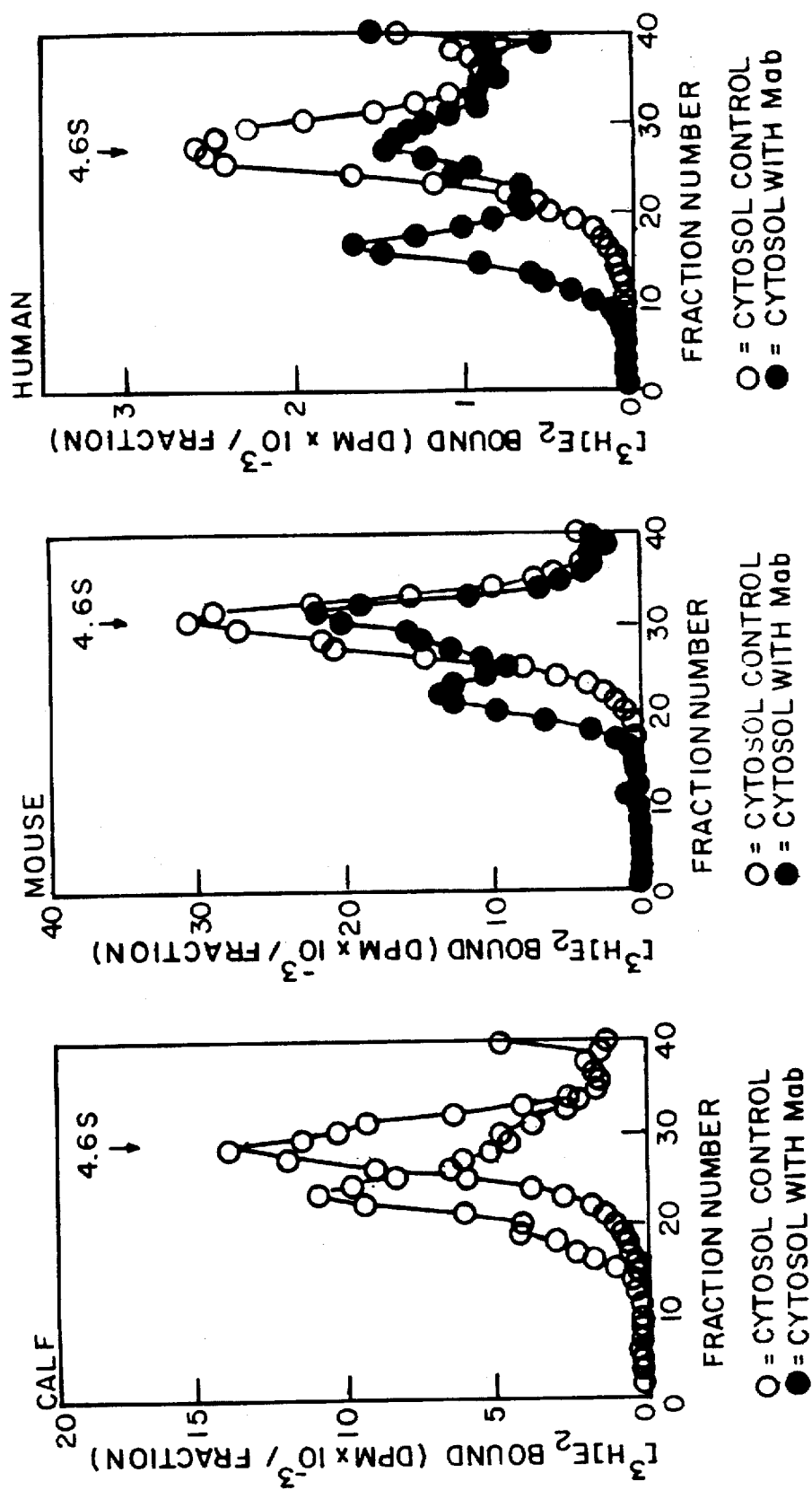

SPECIFIC ANTIBODIES AGAINST AN EPITOPE EXISTING WITHIN THE A/B REGION OF ESTROGEN RECEPTOR PROTEINS

CROSS-REFERENCES

The present invention is a Continuation-In-Part of U.S. Ser. No. 419,975 filed Apr. 7, 1995, now abandoned, which is a Continuation-In-Part of U.S. Ser. No. 243,652 filed May 13, 1994, now abandoned; which is a Continuation-in-Part of U.S. application Ser. No. 784,626 filed Nov. 1, 1991, now U.S. Pat. No. 5,312,752; which is a Continuation of U.S. application Ser. No. 388,091 filed Jul. 31, 1989, abandoned.

FIELD OF THE INVENTION

The present invention is concerned with the development of site-specific monoclonal antibodies raised against preselected functional domains and subdomains within estrogen receptor protein; and is particularly directed to the use of specific monoclonal antibodies directed against individual epitopes and amino acid sequences in the A/B domain of human estrogen receptor protein as a means for evaluating the functionality of estrogen receptors.

BACKGROUND OF THE INVENTION

Breast cancer is the second leading cause of death in women in the United States and is a major health problem. It is estimated that 180,000 new cases will be diagnosed each year, among whom 46,000 deaths will occur. Following removal of the tumor, a number of therapeutic modalities are used presently in management of breast cancer patients, including adjuvant chemotherapy, radiation therapy, endocrine therapy or a combination of such treatments. These treatments have been shown to prolong disease-free survival (DFS) and overall survival of breast cancer patients.

Estrogen receptors (ER) are detected in 50–85% of all breast tumors, a positive ER identifying those patients that have a higher probability of responding to endocrine manipulations. A positive ER content, coupled with presence of progesterone receptors (PR), correlates well with the response rate to hormone modulation. A positive ER also correlates well with tumor histologic differentiation and nuclear grade, but only moderately with S-phase fraction, ploidy and proliferative index.

There is a long recognized and continuing need to identify patients with a higher risk of tumor recurrence in order to improve the management of breast cancer patients. Several prognostic factors are currently used including clinical stage, tumor size, tumor histopathology and nuclear grade, marker of angiogenesis (factor VIII), tumor ploidy and proliferative rate, and ER and PR content. ER content, coupled to PR levels, is thought to provide a useful prognostic index in patients with metastatic tumors. However, in spite of this correlation, only about 65% of all patients with ER+ tumors respond to endocrine treatment.

It is useful therefore to understand the role of estrogen receptor protein as such. Note that the presence of intracellular ER provides and accounts for both cell proliferation and new protein synthesis by estrogen dependent cells. The estrogen receptor in the absence of the estrogen hormone is biologically inactive both in vivo and in vitro; and, if the cells or tissues are homogenized and fractionated into cytosol and nuclear fractions, the estrogen receptor is found as a soluble protein in the cytosol.

Although the precise mediators and reactions remain poorly understood, the generally accepted mechanism of action and sequence of events for ER interactions is believed to be as follows: When an estrogen (such as estradiol) is introduced to the target cells and tissues, there is specific binding between the estrogen and the ER protein which results in the formation of an estrogen/receptor protein complex. Also, at a time subsequent to such hormone binding, a process termed "activation and/or transformation" ensues which leads to the formation of functional estrogen/hormone receptor complexes having a high affinity for the nuclear components, the DNA, of the target cell. Once the hormone-receptor protein complex is physically formed, it is thought to translocate as a complex into the nucleus of the cell where it binds to the chromatin at specific binding sites on the chromosomes and initiates messenger ribonucleic acid (mRNA) transcription. New mRNA is then synthesized, chemically modified, and exported from the nucleus into the cytoplasm of the cell where ribosomes translate the mRNA into new proteins. This is the well recognized "estrogenic effect" on the cell—that is, the initiation of new protein synthesis and concomitant new cell growth/proliferation. The theoretical premise and the generally accepted, though poorly understood, mechanism of action regarding estrogen and estrogen receptor proteins and their interactions are described in greater detail by the following publications which are merely representative of the ongoing investigations in this field. These are: Mestre et al, Exp. Cell. Res. 81:447–452 (1973); King and Greene, Nature 307:745–747 (1984); Welshons et al., Nature 307:747–749 (1984); Gorski and Gannon, Annu. Rev. Physiol. 38:425–450 (1976); Gorski et al., Recent Prog. Horm. Res. 24:45–72 (1968); Jordan, V., Pharmacological Reviews 36:245–276 (1984).

In order to truly appreciate the significance and value of the present invention, it is useful to summarize the major details regarding the different structural isoforms and functional states for the intracellular protein known as estrogen receptor. In the unbound state and in the absence of an estrogen, the estrogen receptor protein can be located in vitro within the cytosol and is a single protein composed of 595 amino acids. The molecular weight of ER protein determined from gel electrophoresis and other physical methods is approximately 67,000 daltons. In soluble systems and under set test conditions, the ER protein can be found in alternative molecular forms or isoforms which sediment at either 8S, 5S, or 4S as determined by sucrose density gradient analysis. The 8S isoform of ER is believed to be the unactivated, untransformed form of the ER protein and is associated with the unbound, inactive state of estrogen receptor in the absence of estrogens. The 8S ER isoform is a large molecular weight complex, presumably associated with heat shock proteins, that does not bind efficiently to nuclei or DNA in vitro and is stabilized as a macromolecule by sodium molybdate.

In comparison, the 4S ER isoform is a monomeric protein molecule that can be generated from the 8S isoform in vitro by treatment with high ionic strength buffers or by increasing salt concentrations (KCl or NaCl). The 4S ER isoform binds to both nuclei and DNA-cellulose in vitro; it is generally termed the "activated but untransformed" estrogen receptor protein. From the published reports, it appears that the dissociation of the 8S ER isoform into the 4S isoform initiates either a major change in the sterochemical conformation of the protein or a direct exposure of the previously hidden or obscured DNA binding domain of the molecule.

Alternatively, the 5S isoform of ER is a dimeric protein molecule created by the conversion of the 4S ER protein via a bimolecular reaction which is facilitated by elevated temperatures and/or dilution after KCl activation. The 5S form of ER can be generated in vitro by incubation of either the 8S or 4S isoforms at 28°–30° for 30–45 minutes in the absence of transformation inhibitors. It is generally believed that the 5S isoform of ER is both "activated and transformed" and therefore is the biologically active entity which binds to the DNA within the nuclei. Moreover, it is also this 5S isoform which is found associated within the nuclei subsequent to the administration of estradiol in vivo.

It will be appreciated that the present state of knowledge regarding the various forms of estrogen receptor protein have been obtained and characterized via many different investigations, many of which employ physical an chemical structural and isoform analysis. Merely representative of such investigations and reports are the following: Muller et al., *Endocrinology* 116:337–345 (1985); Muller et al., *J. Biol. Chem.* 258:11582–11589 (1983); *Endocrinology of the Breast: Basic and Clinical Aspects*, Volume 464, Annals Of the New York Academy of Sciences, pages 202–217, 1986; Parmer et al., *J. Steroid Biochem.* 31:359–364 (1988); Traish et al., *J. Biol. Chem.* 255:4068–4072 (1980); and Muller et al., *J. Biol. Chem.* 257:1295–1300 (1982).

Recent reports on the cloning of the complementary DNA for steroid receptors also have generated new information concerning the functional domains of steroid receptors. Functional studies have delineated the putative roles of several domains; and these studies have demonstrated that the estrogen receptor (ER) consists of multiple functional domains which provide and are responsible for the characteristic biological and physiological properties individually. The complementary DNA (cDNA) of human estrogen receptor also has lead directly to the elucidation of the human ER protein primary amino acid sequence.

The multiple functional domains of human ER protein provide six individual and distinctive regions, each of which provides different properties and characteristics. Each of the six functional domains have been designated as regions "A–E" respectively. The N-terminal domain comprising regions A and B together span the first 184 amino acids of ER proteins; and have yet to be assigned a precise function in gene expression, although it is postulated that they are required for full functional activity in certain types of cells or for interaction with specific kinds of genes.

Specifically, the A/B region or domain contains a transactivation subdomain (TAF-1) and is thought to be the amino acid segment important for gene and cell specificity. Mutations in the A/B domain have been shown to impair expression of ER responsive genes. Thus, receptors with an altered or modified A/B region can fail to produce any biological function or mass produce an abnormal function.

The third functional domain is region C which encompasses the amino acid segment 185–263 of human ER and is necessary for the binding of ER to genomic DNA to occur. In particular, the DNA-binding domain is also involved in nuclear translocation, dimerization and transactivation; and it has been shown that deletion of DNA-binding region, or mutations in the dimerization domain or the transactivation domains eliminated ER function. Thus, any truncation or mutation of this C domain will lead to inactive (nonfunctional) ER.

Less is known presently about the other three domains of ER protein. Region D (position Nos. 264–302) is believed to be the hinge area of the protein with as yet an undefined function. It has been shown that alterations in this region did not affect ER function.

Region E (position Nos. 303–552) is believed to be the steroid binding domain because this region comprises an amino acid sequence which is generally shared between different classes of receptors for steroids. Region F (position Nos. 553–595) has yet to be assigned a specific function.

It is important to note that regions C and E are said to be conserved among all the steroid receptor family members throughout the different animal and human classes—thereby indicating that these particular domains or regions are deemed to be critical for hormone receptor function generally within steroids as a family. Specific publications describing these investigations, data, and conclusions in greater detail are represented by the following: Kumar et al., *Cell* 51:941–951 (1987); Hill et al., *Cancer Res.* 49:145–148 (1989); Greene et al., *Nature* 320:134–139 (1986); and Greene et al., *Science* 231:1150–1153 (1986).

It is also essential to understand the relationship between domain or region and structure and biological function; and to realize that structural alteration(s) in ER may interfere with normal ER activity by reduction or inhibition of characteristic biological functions. Alternatively, an altered ER may be constitutively active in transacting of $E_2$-responsive genes. Several studies have reported the presence of altered/nonfunctional ER in human breast tumors. A number of ER variants (ERVs) in breast tumors have been described, including those with base-pair insertions, deletions and transitions or those with mutations in DNA-binding C domain or in the hormone-binding E domain. These ERVs may have intrinsically impaired function or may influence ER function through positive or negative dominance, contributing to hormone insensitivity.

Functional studies have also shown that deletion of the DNA-binding region or mutations in the dimerization and transactivation domains eliminates ER function without affecting $E_2$-binding activity. Alteration of ER DNA-binding activity in breast tumors and in the T47D breast cancer cell line have recently been described. Wang and Miksicek have reported the isolation of two ER mRNA variants in T47D human breast cancer cells which have deletions in the DNA-binding domain. These ERVs inhibit estrogen-dependent transcriptional activation by wild-type ER in a negative-dominant fashion.

Also Faqua et al. [*Cancer Res.* 51:105–109 (1991)] have described an ERV in breast tumor missing the hormone-binding region which exhibits positive dominance and may explain the continued expression of PR in some ER-tumors. Another variant expressed in ER+/PR– tumors exhibits negative-dominance. Katzenellenbogen et al. [Programs+ Abstracts Endo. Soc., p. 289, No. 953, 1993] have shown that three ER mutants, generated by random chemical mutagenesis, interfere with normal ER function.

Clinically, the functional role of ER and the hormonal treatment of ER+ tumors is far less known or understood. The use of estrogens such as estradiol in hormonal therapy fails in about 35% of patients with ER+ tumors. The lack of response to hormonal manipulations has been attributed, at least in part, to: (a) the presence of nonfunctional ER as determined by its inability to recognize and bind to specific DNA-responsive elements and/or its inability to recruit other transcriptional activation factors; (b) tumor heterogeneity in which some tumor cells may contain functional ER while other cells may contain either dysfunctional ER or do not express ER at all and may become autonomous with respect to their hormone sensitivity, allowing tumor progression; and/or (c) mutations of specific estrogen-responsive genes, thus affecting gene expression.

In addition, several tumor phenotypes have been described based on ER and PR content; and the ERVs described above influence the behavior and hormone sensitivity of these tumors. For example, ER+/PR+ tumors may express both functional and nonfunctional ER, which could serve to explain incomplete sensitivity to endocrine manipulations. Also, ER+/PR− tumors may have ER with altered DNA-binding or transactivation domains and, thus fail to transactivate $E_2$-responsive genes; ER−/PR+ tumors may have ER with an altered hormone-binding domain but remain constitutively active; and ER−/PR− tumors may not express ER or be defective in one or more domains and, consequently, may be transcriptionally inactive.

Via these many different published reports, it will be noted and appreciated also that currently available diagnostic tests to determine the presence or absence of ER protein in tumors (and the many assays employed for research purposes regarding ER protein) depend and rely either on binding of ligand to the receptor protein in cell extract or upon the existence of specific antibodies raised against ER. A variety of different polyclonal antisera have been prepared against estrogen receptor protein and against the nuclear binding estradiol-receptor complex typically identified as "estrophilin" [Raam et al., *Mol. Immunol.* 18:143–156 (1981); Greene et al., *J. Ster. Biochem.* 11:333–341 (1979); Greene et al., *Proc. Natl. Acad. Sci. USA* 74:3681–3685 (1977)]. Similarly, a large number of monoclonal antibodies against human and animal estrogen receptor proteins and estrophilins have been prepared for many different investigational purposes [Greene et al., *Proc. Natl. Acad. Sci. USA* 74:3681 (1977); Green et al., *Proc. Natl. Acad. Sci. USA* 77:157–161 (1980); Greene et al., *Proc. Natl. Acad. Sci. USA* 77:5515 (1980); Brogna et al., *Biochem.* 23:2162–2168 (1984); Fauque et al., *J. Biol. Chem.* 260:15547–15553 (1985); and Moncharmont et al., *Biochemistry* 23:3907–3912 (1984)].

The common flaw and recurring problem of these known polyclonal and monoclonal antibodies against ER is their uniform and consistent failure to be site specific. This failure, in turn, produces erroneous empirical results and unreliable information—not only for investigational purposes but also in clinical applications of such antibodies for diagnostic/therapeutic purposes. As a major example, the measurement of estrogen receptors in human breast carcinomas has been the primary tool and favored diagnostic method for choosing between hormonal and cytotoxic chemotherapy when treating breast cancer patients. A variety of different immunoassays employing anti-ER antibodies are presently known and used for this purpose. These are exemplified by the following publications: U.S. Pat. Nos. 4,232,001; 4,293,536; 4,215,102; and 4,711,856. See also European Patent Application Publication No. A2-0129669 published Jan. 2, 1985. Unfortunately, the immunoassays employing conventionally obtained monoclonal antibodies for these measurements have been found to be frequently unreliable and often non-specific. The nature and variety of problems of these unreliable and non-specific monoclonal antibodies are illustrated by the following publications: Raam, S. and D. M. Vrabel, *Clin. Chem.* 32:1496–1502 (1986); Raam, S. and D. M. Vrabel, *Clin. Chem.* 34:2053–2057 (1988); Raam, S., *Steroids* 47:337–340 (1986); and Raam, S., *Clin. Chem.* 22:1107–1108 (1987). Clearly, therefore, given all the presently known antibodies, assays, and immunological techniques, one still cannot accurately predict which of the estrogen receptor positive tumors will respond to hormonal treatment.

The causes of the present dilemma are in fact two-fold: First is the failure of the monoclonal antibodies and polyclonal antisera to be sufficiently site-specific in order to demonstrate the presence of estrogen receptor in its various multiple forms. Second is the failure (in so far as is presently known) of these conventionally known antibodies to differentiate between functional and nonfunctional ER.

Currently, human breast tumor estrogen receptor (ER) values are used as prognostic factors in determining treatment of breast cancer patients with tamoxifen. ER content in tumor tissue is usually determined by either radioreceptor assays or immunochemical techniques. Binding of labeled estrogen hormone (ligand) to ER does not provide sufficient information concerning the structural or functional integrity of the DNA-binding domain or the transactivation function located in the A/B region of the receptor. Similarly, immunochemical or immunocytochemical analysis, in soluble fractions or in fixed tissue sections, using antibodies with undefined binding epitopes do not provide information on the functional domains of ER.

It is now clearly apparent to practitioners and clinicians ordinarily skilled in this art that so long as these insufficiently specific antibodies remain in clinical use, many repetitive failures in the known immunoassay systems will occur; and the ability to identify that proportion of breast cancer patients which would be sensitive and responsive to estrogen hormonal treatment will remain plagued with uncertainty and inaccuracy. For these reasons, the development of site-specific antibodies common to the transactivating A/B domain of ER and their use within conventionally known diagnostic immunoassays would therefore be recognized generally as a major advance and fundamental improvement in antibody materials, assay reliability, and therapeutic benefit.

SUMMARY OF THE INVENTION

The present invention has multiple aspects and parts which are intimately related.

A first aspect of the invention provides a monoclonal antibody specific for epitope within amino acid residues 1–184 of an estrogen receptor protein, said monoclonal antibody having binding specificity for a single epitope within the A/B domains in the activated but untransformed (4S) forms and in the activated and transformed (5S) forms of estrogen receptor protein but which does not bind with native (8S) forms of estrogen receptor protein.

A second aspect of the present invention provides a hybridoma which produces a monoclonal antibody specific for an epitope within amino acid residues 1–184 of an estrogen receptor protein, said hybridoma comprising:

an antibody producing cell producing a monoclonal antibody having binding specificity for a single epitope within the A/B domains in the activated but untransformed (4S) forms and in the activated and transformed (5S) forms of estrogen receptor protein but which does not bind with native (8S) forms of estrogen receptor protein; and a tumor cell fused with said antibody producing cell.

DETAILED DESCRIPTION OF THE FIGURES

The present invention may be more easily and completely understood when taken in conjunction with the accompanying drawing, in which:

FIG. 1B recites the full length nucleotide sequence and deduced amino acid sequence of MCF-7 estrogen receptor mRNA;

FIGS. 7A, 7B and 7C are graphs illustrating the specie specificity of anti-NMT-1 monoclonal antibodies in calf uteri, mouse uteri, and human breast cancer cytosols;

DETAILED DESCRIPTION OF THE PREFERRED EMBODIMENTS

Figure 1A:
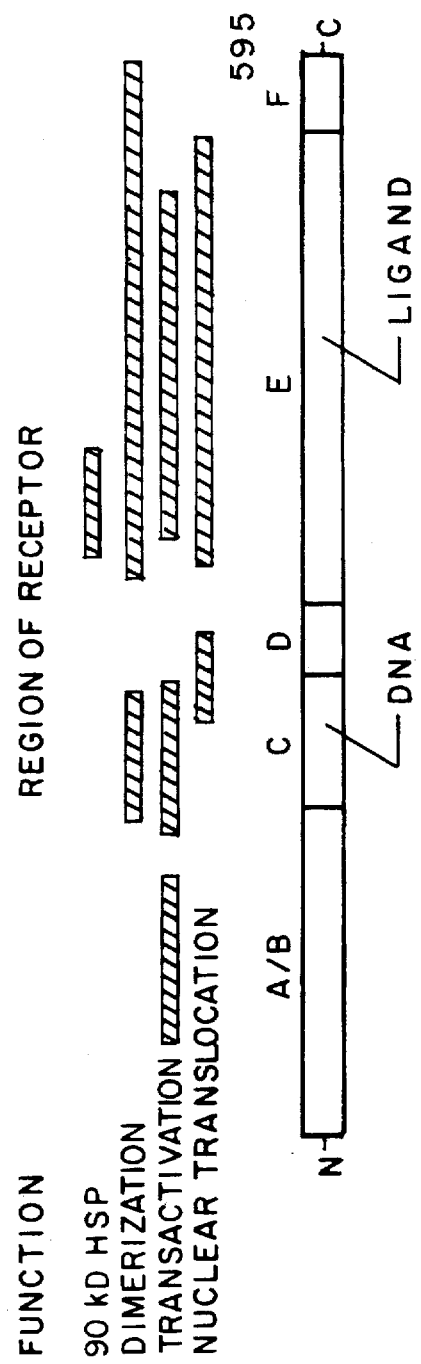
FIG. 1A illustrates the human estrogen receptor structures.
Figure 2A:
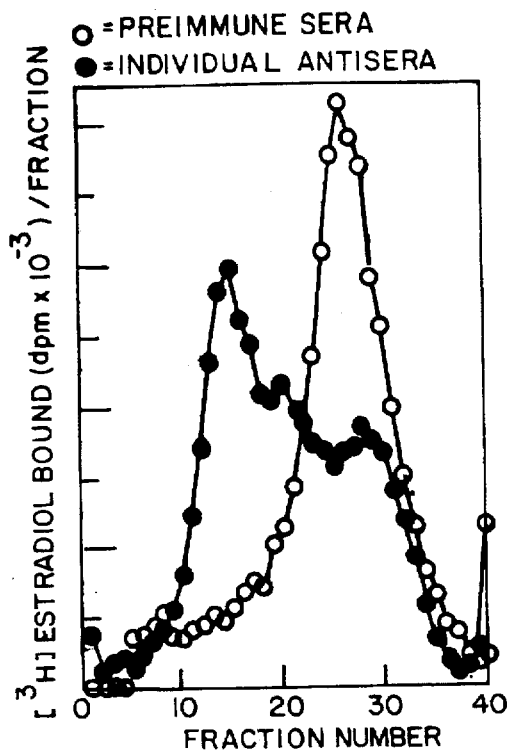
FIGS. 2A, 2B, 2C and 2D are graphs illustrating the binding of mouse polyclonal antibodies generated against peptide NMT-1 to estrogen receptor in calf uterine cytosol.
Figure 2B:
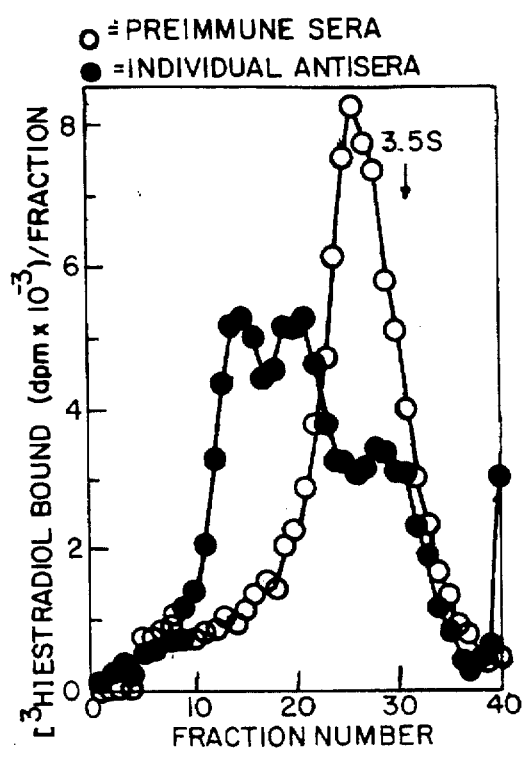
Figure 2C:
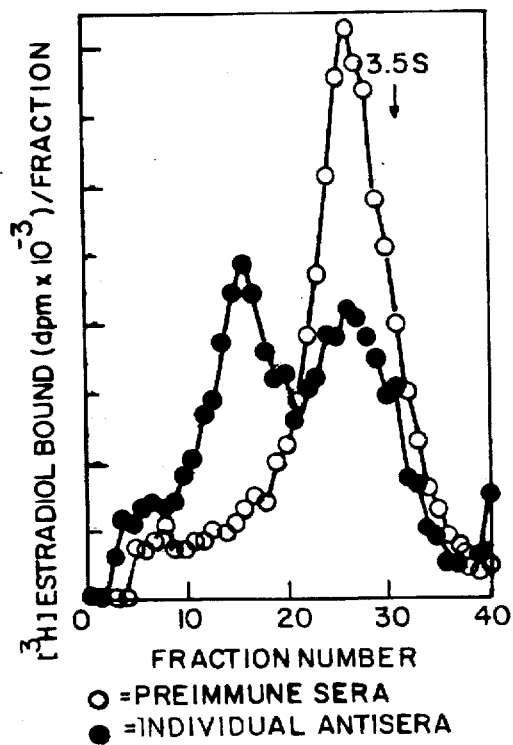
Figure 2D:
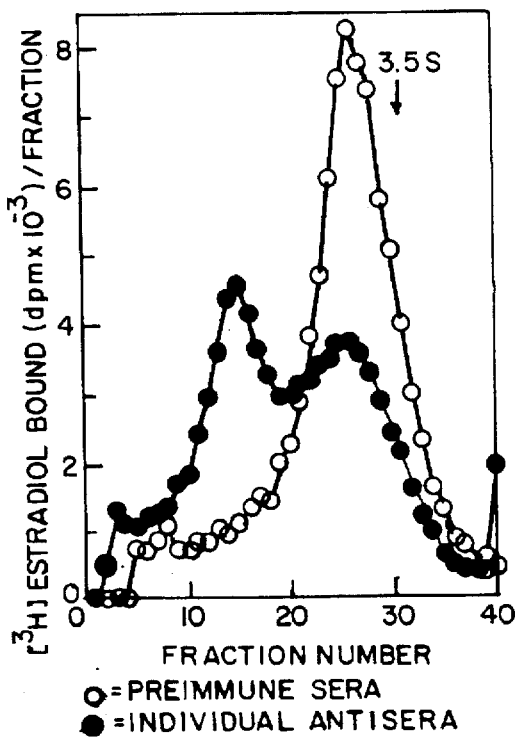
Figure 3A:
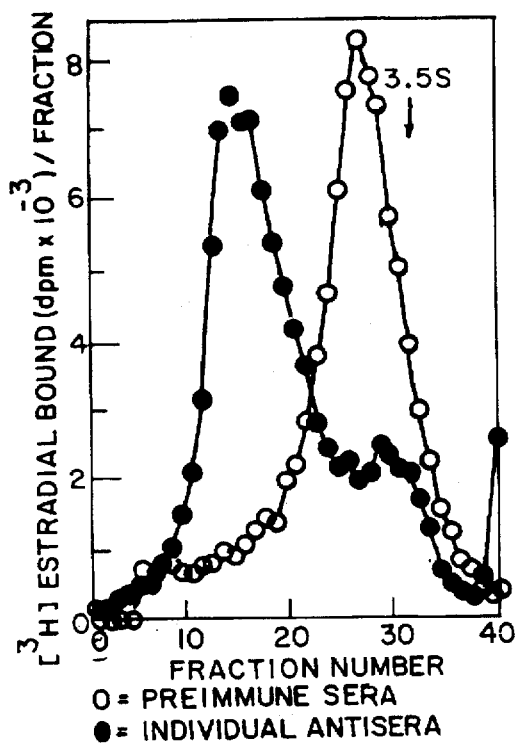
FIGS. 3A, 3B, 3C and 3D are graphs illustrating the binding of anti-NMT-2 mouse polyclonal antibodies to estrogen receptor in calf uterine cytosol.
Figure 3B:
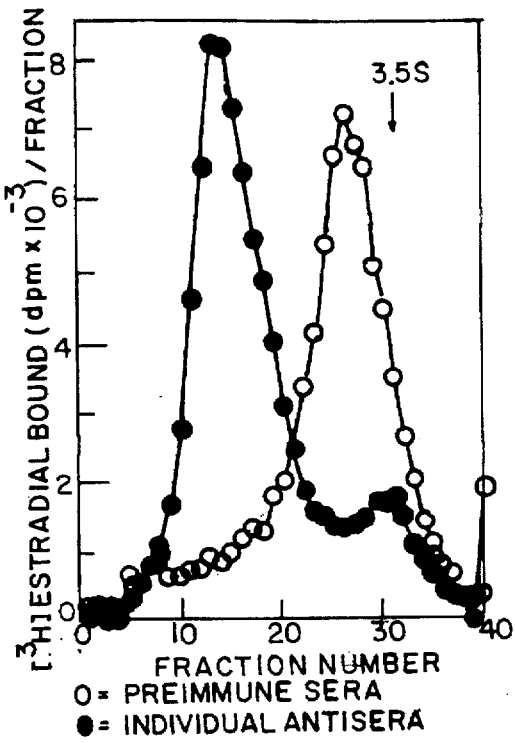
Figure 3C:
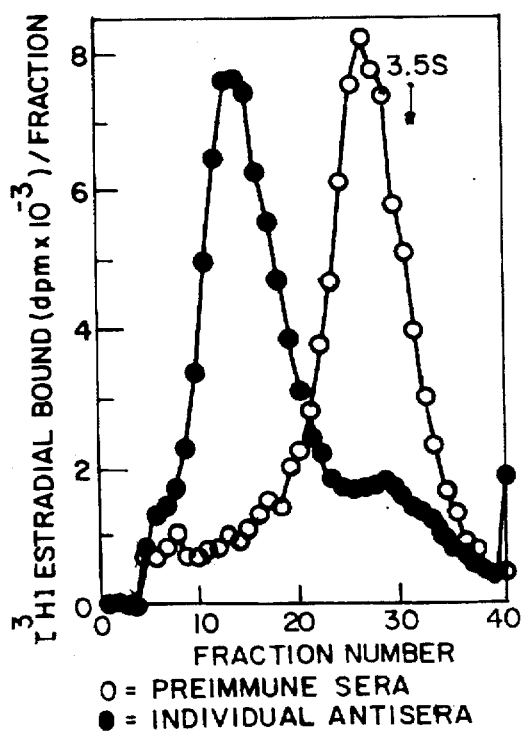
Figure 3D:
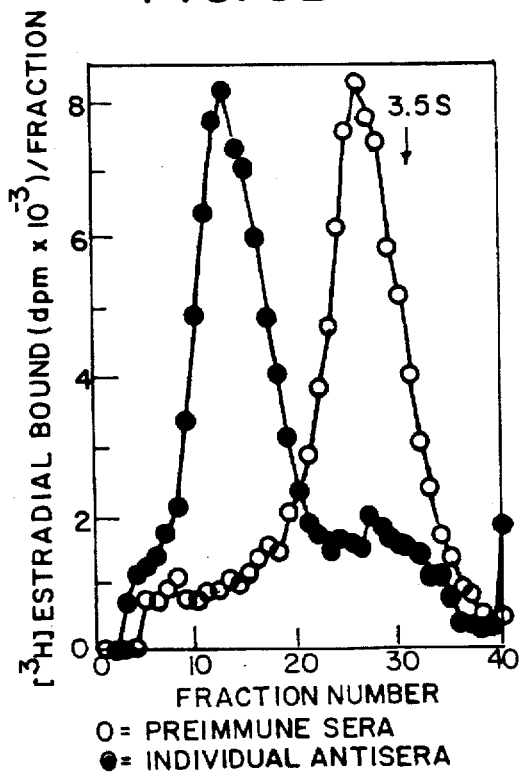
Figure 4A:
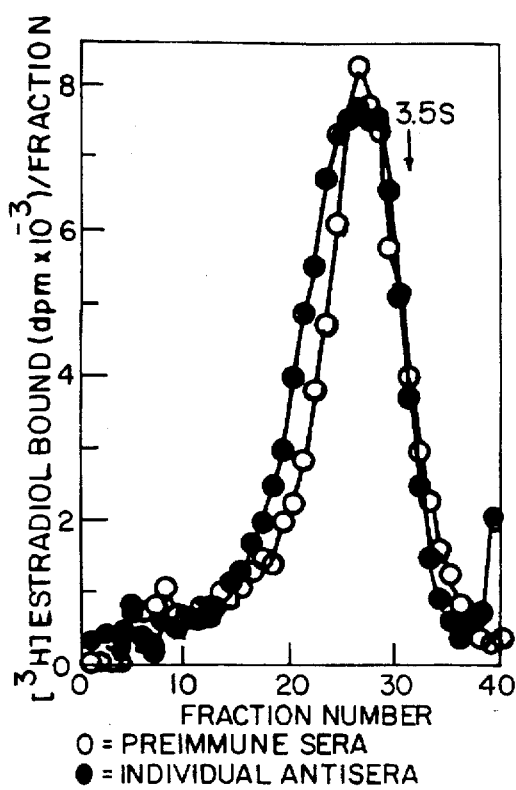
FIGS. 4A, 4B, 4C and 4D are graphs illustrating the binding of anti-NMT-3 mouse polyclonal antibodies to estrogen receptor in calf uterine cytosol.
Figure 4B:
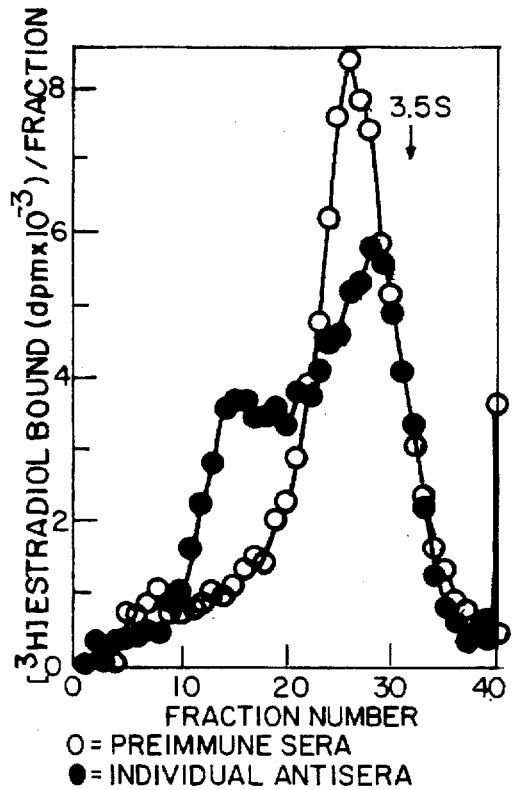
Figure 4C:
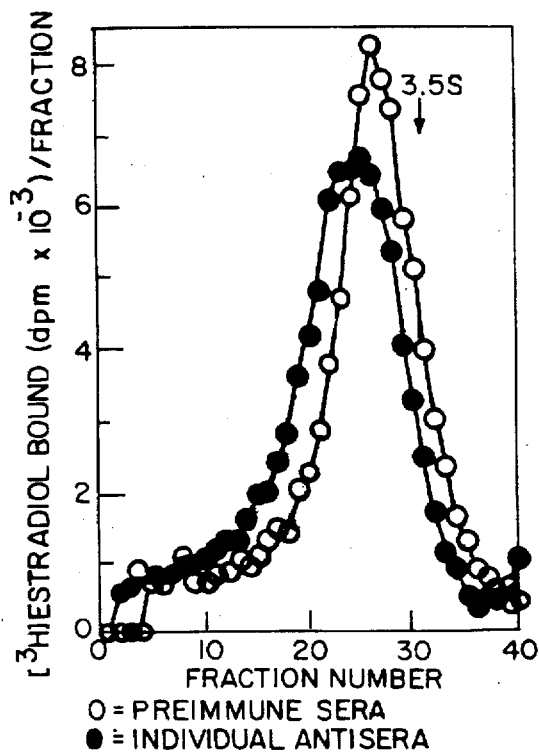
Figure 4D:
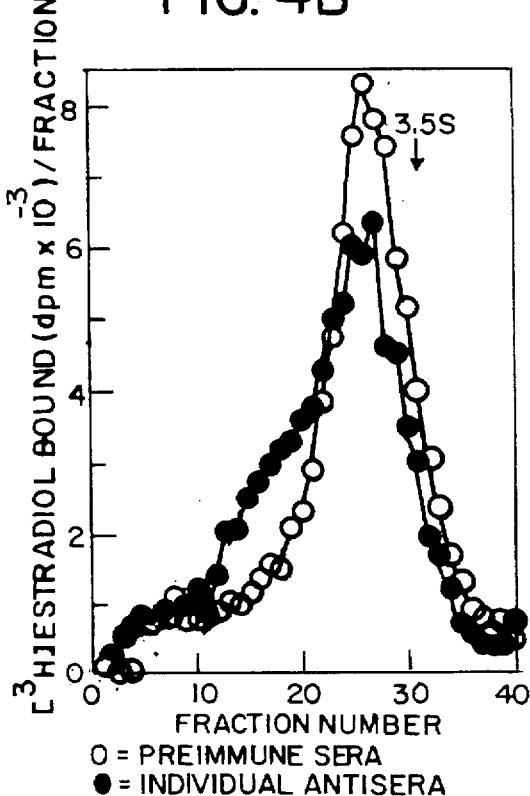

The present invention as a whole is based upon the unique approach of developing site-specific polyclonal and monoclonal antibodies against the transactivating A/B domains of estrogen receptor protein. The polyclonal antisera and the monoclonal antibodies are used to identify the presence or absence of an intact transactivating A/B domain within the ER sample under test; and to differentiate between functional and nonfunctional states of estrogen receptor in vitro. On this basis the user is able to determine whether the A/B domain of the ER is structurally intact and present in a functional or non-functional state. The invention, therefore, includes specifically prepared immunogens; polyclonal antisera and epitope-selective monoclonal antibodies which bind specifically to the A/B domain; and immunoassays employing these site-specific antibodies with cellular samples on a functional and correlative test basis.

It will be noted and appreciated that the present invention overcomes several major impediments and problems normally encountered in the production and use of specific antibodies. These benefits and advantages include:

1. Since oligopeptides of known amino acid sequence are employed as the hapten within the prepared immunogen, there is no longer any need for purification of ER, particularly human ER, for immunization purposes; thus a task which normally requires large resources and considerable amounts of tissue is eliminated.

2. The present invention allows the user to select the precise domain and/or subdomains intended to be the specific binding site for the antibody about to be produced. Previous approaches and techniques utilized either the whole estrogen receptor protein or the complete hormone/receptor complex as the immunogen—neither of which provides any site specificity properties or capabilities whatsoever.

3. The present invention precludes the binding of the site-specific monoclonal antibody to an ER protein when existing in an altered, non-functional state and is unable to undergo activation/transformation.

To fully appreciate the present invention, it is useful to focus on a single kind of estrogen receptor protein, recognizing that the characterization of the one ER may properly be extended to include all other types and sources of ER protein generally. For this reason, the remainder of this description and the experiments and empirical data which follow hereinafter are limited to the use of human estrogen receptor (hereinafter "hER"). For this purpose also, all the presently available information regarding the primary amino sequence and the various functional domains of human estrogen receptor protein have been employed. Nevertheless, it will be clearly and explicitly understood, that the scope of the present invention encompasses the ability to prepare site-specific antibodies against individual domains and subdomains of ER from all presently known sources and origins, whether human or animal.

I. GENERAL PREPARATION, REAGENTS, REACTIVE MIXTURES, AND TESTING PROCEDURES

A detailed general description follows disclosing the means and manner generally of preparing oligopeptides, immunogens, immunization practices, preparation of hybridomas, and the isolation of epitope-specific monoclonal antibodies. These procedures recite and delineate the compositions and methods by which the ordinarily skilled practitioner in this art can make and use the antibodies of the present invention to advantage, without incurring substantive difficulties.

OLIGOPEPTIDES

As regards the domains of human ER protein and its different functional states, it will be recognized that the human receptor molecule is a single polypeptide having 595 amino acids in sequence in which the A and B regions include the amino acid segment from about positions 1–184 respectively. These domains are a critical region of the human ER; the A/B regions provides the transactivating capability in vivo for the entire ER molecule. Therefore, each domain individually (A or B region alone) or collectively (A/B together) can provide at least a portion or fraction of the amino acids useful as fused oligopeptides which can then serve as haptens for raising site-specific antibodies in accordance with the present invention.

As described in detail hereinafter, oligopeptides having known amino acid sequences identical to chosen segments within positions 1–184 of human estrogen receptor ("hER") were prepared and purified. These individual oligopeptides were first linked to an antigenic protein carrier (such as keyhole limpet hemocyanin); and then were used as prepared immunogens to produce antibodies to the DNA-binding domain specifically. For purposes of practicing the present invention, however, it is not necessary that all these specific hER amino acid residue sequences be employed when preparing the immunogen. To the contrary, for human purposes, it is required only that an immunogenic oligopeptide be chosen whose amino acid residue sequence corresponds to at least one epitope commonly present within the entire 1–184 amino acid residues which encompass the A and B regions of hER. Any amino acid segment able to function as a hapten and thereby provide one specific epitope or site-specific binding capability for the resulting antibody is thus suitable for use. Moreover, although the characterized oligopeptides average approximately 15–30 amino acid residues in length, there is no requirement that any polypeptide sequence conform to this particular length or size for purposes of preparing the immunogen. In general, however, it is desirable that the oligopeptide representative of an ER subdomain be at least about 5–7 amino acid residues in number as the minimum segment size able to serve as a hapten. Nevertheless, any number of amino acid residues in sequence which is or represents a specific epitope of these domains and is able to provide the necessary hapten attributes and site-specificity for the prepared immunogen is suitable and deemed to be within the scope of the present invention.

In addition, although it is desirable that the amino acid residue sequence of the chosen oligopeptide be in fact identical to the true, naturally occurring amino acid sequences of the A/B region, this is not an absolute requirement. To the contrary, it is expected that substantial variation of the amino acid residues which differ from those normally found within the A/B regions of the hER molecule is permissible; nevertheless, it is most desirable for the chosen amino acid sequence to be completely or very nearly identical to the sequences normally existing in the A/B domains, particularly when the oligopeptide is of a minimal length and size.

Synthesis Of Oligopeptides

The oligopeptides employed herein were prepared using conventionally known solid phase peptide synthesis methods [Merrifield, R. B., J. Am. Chem. Soc. 85:2149 (1963)]. Once synthesized, the individual oligopeptides were purified by gel filtration and analyzed for purity by HPLC. Analysis of the amino acid composition correlated well with the primary sequence. Each peptide contained one [$^3$H]-labeled amino acid as a tracer. This provided the means for determining the efficiency of coupling to the various carrier proteins.

Reagents

Isotopes and Chemicals

[6,7$^3$H] estradiol (40–60) Ci/mmol) ([$^3$H]E$_2$), 7α, 17 α-dimethyl [17α-methyl $^3$H]-19-nortestosterone (70–85 Ci/mmol) ([$^3$H] DMNT) 16 α-ethyl-21-hydroxy-19-nor [6,7$^3$H]-pregn-4-ene-3,20-dione (40–60 Ci/mmol) ($^3$H] ORG 2058), [$^3$H]-triamcinolone acetonide (20–40 Ci/mmol) ($^3$H]TA), unlabeled DMNT, and ORG 2058 were obtained from Amersham, Arlington Heights, Ill. Unlabeled TA was obtained from Sigma Chemical Co., St. Louis, Mo., unlabeled diethylstilbestrol (DES) and E$_2$ were obtained from Steroids, Wilton, N.H. All other chemicals were reagent grade and were obtained from commercial sources.

Buffers and Solutions

Buffer TGT: 50 mM Tris-HCl, 10% glycerol, 10 mM thioglycerol (pH 7.4 at 2° C.).

Buffer TGT/MO: buffer TGT with 10 mM sodium molybdate.

Buffer TT: 50 mM Tris-HCl, 10 mM thiolglycerol (pH 7.4 at 2° C.).

Buffer TT/KCl: buffer TT containing 0.4M KCl.

IMMUNOGENS

After an oligopeptide has been synthesized, it is then chemically coupled to a protein carrier to form the prepared immunogen. The suitable protein carriers available for this purpose are conventionally known and available in great variety from diverse sources. The only requirements regarding the characteristics and properties of the carrier protein are: First, that the carrier be in fact antigenic alone or in combination with the chosen oligopeptide; and second, that the carrier protein be able to present the chemically bound oligopeptide after administration in vivo such that antibodies specific against at least one epitope present concurrently or shared between the A and/or B domains of the ER molecule are produced. Clearly, as in the experiments described hereinafter, the preferred choice of protein carrier for immunization purposes was keyhole limpet hemocyanin (hereinafter "KLH"). However, any other carrier protein compatible with the host to be immunized is also suitable for use. Examples of such other carrier proteins include bovine serum albumin, gelatin, thyroglobulin, and the like.

Coupling Of Oligopeptides To Carrier Proteins

To prepare effective immunogens, the oligopeptides were individually coupled to known carrier proteins to form antigenic immunogens. The carrier proteins of choice were keyhole limpet hemocyanin and bovine serum albumin (hereinafter "BSA"). The KLH-coupled peptides were used as immunogens while the BSA-coupled peptides were used only for screening assays. This coupling procedure was performed as follows.

KLH and BSA were dissolved in phosphate buffered saline (PBS: 0.2 g KH$_2$PO$_4$, 8 g NaCl, 2.16 g Na$_2$HPO$_4$ 7H$_2$O in one liter of distilled water, pH 7.5) to give a final concentration of 1 mg/ml. One hundred mg of each peptide was then dissolved in 10 ml of KLH solution and 50 mg of each peptide was dissolved in 5 ml of BSA solution. The pH of the mixtures was adjusted to 9 with 0.1M LiOH. The coupling of the peptides to the carrier proteins was initiated by dropwise addition of 6.25% glutaraldehyde to achieve a final concentration of 1% glutaraldehyde. Each mixture was then incubated at 0°–4° C. for 1 hour with gentle agitation. Aliquots (50–200 ul) were then removed and used to determine total peptide concentration by radioactivity counting. The remainder of each mixture was then transferred to dialysis tubes and dialyzed extensively against four changes of PBS. Aliquots were then removed after dialysis and counted to determine the efficiency of coupling. The remaining dialyzed material was divided into 1 m. aliquots and frozen at −80° C. until needed.

Immunization Procedures

All immunizations and immunization procedures are performed in the conventionally known manner. It is expected that under certain use conditions, adjuvants will be employed in combination with the prepared immunogens. Alternatively, the prepared immunogens may be used alone and administered to the host in any manner which will initiate the production of specific antibodies.

In addition, the harvesting of polyclonal antiserum and the isolation of antibody containing sera or antibody producing cells follows the conventionally known techniques and processes for this purpose. Similarly, the preparation of hybridomas follows the best practices developed over recent years for this specific purpose [Marshak-Rothstein et al., *J. Immunl.* 122:2491 (1979)]. A complete detailed description of the preferred techniques and procedures follows hereinafter.

Immunization Of Rabbits

New Zealand white female rabbits (7–9 lbs) were used. Prior to immunization, serum was collected from each rabbit by bleeding through the ear artery and designated as pre-immune serum. One day later each animal was injected subcutaneously at multiple sites along the back with a total of 1 ml of an emulsion made by mixing equal volumes of complete Freund's adjuvant and KLH-conjugated peptide mixture. The final emulsion contained 1 mg/ml of the desired peptide. After three weeks the rabbits were boosted with the antigen in incomplete Freund's adjuvant. Two weeks after the booster shots, the rabbits were bled and the sera collected and tested for the presence of peptide-specific antibodies by enzyme-linked immunoabsorbent assay (ELISA). The animals were then given booster shots several times and bled 14 days after the final booster. This procedure provided all the peptide-specific polyclonal antisera described hereinafter.

Immunization Of Mice

In addition, groups of female mice [(BALB/cA/J $F_1$] 6–8 weeks old were also immunized by injecting s.c. 100 ug of the designated oligopeptides, emulsified in Freund's complete adjuvant. Two s.c. booster injections were given at 3 week intervals. The mice were bled through the vein and the sera were tested for antibodies by sucrose density gradient analysis. Those mice which appeared to have antibodies against ER were then selected. After one month of rest the mice were given 100 ug of the antigen in PBS intraperitoneally (i.p.) and sacrificed three days later; then their spleens were removed and used for cell fusion and the production of monoclonal antibodies.

ANTIBODIES

Preparation Of Hybridomas And Isolation Of Monoclonal Antibodies

Cell fusion was carried out by the method of Marshak-Rothstein et al. [*J. Immunol.* 122:2491 (1979)]. Briefly, mouse spleens were excised; the fat and mesenteric tissues were removed quickly; and a single cell suspension was made by squeezing the spleen between two glass slides in Hank's balanced salt solution (HBSS) buffered with 0.02M phosphate, pH 7.2. Red blood cells were lysed by brief incubation in ammonium chloride lysis buffer. Spleen cells ($5\times10^7$ cells) were mixed with Sp 2/0 cells ($5\times10^6$ cells) in round bottom tubes and pelleted at 700×g for 5 min at 22° C. The cells were resuspended in serum-free DME and centrifuged. After removal of the supernatant, the cell pellet was resuspended for six minutes in 0.5 ml of polyethylene glycol 1,500 ("PEG", 30% v/v) Baker Chemical Co., Phillipsburg, N.J.), followed by addition of 4 ml of serum free DMEM (Dulbecco's Modified Eagle's Medium) to dilute out the PEG. The cell suspensions were transferred into petri dishes (100×17 mm) and DME containing 20% FCS (fetal calf serum) was added and the cultures were kept at 32° C. for 24 h under 5.6% $CO_2$. The cells were then pelleted and resuspended in HAT (hypoxanthine, aminopterin, and thymidine) conditioned medium ($1\times10^6$ cells/ml). Aliquots of the cells suspension (0.1 ml) were dispensed into 96-well flat bottom microtiter dishes and incubated at 37° C. Seven days later the hybridoma cells were treated with 0.1 ml of conditioned media (DME, HT). After another two days, the resulting hybridomas were screened by enzyme-linked immunoabsorbent assay (ELISA) against BSA-conjugated oligopeptides.

The isotype of each monoclonal antibody was determined by ELISA. Microtiter plates coated with the immunogenic oligopeptide were incubated with aliquots of the spent media from the hybridoma. Bound antibody heavy chain class was determined by addition of goat-antimouse isotyping reagents (Southern Biotech, Birmingham, Ala.) diluted 1:1,000 in PBS-0.2% BSA, followed by alkaline phosphatase conjugated rabbit-antigoat secondary antibody and the substrate.

Hybridoma clones that tested positive by ELISA were recloned by limiting dilution. Cells were diluted to 1, 0.3, 0.1 cell equivalent/ml in DMEM containing 2% FCS and BALB/c peritoneal exudate cells ($5\times10^4$ cells ml) and then plated in 96-well microtiter plates. After ten days, wells with single hybridoma clones were identified by microscopic examinations and tested for presence of antibodies by ELISA. Clones that tested positive were expanded in large flasks, spent media were collected, and cells were either used for ascites productions or frozen for later use.

Polyclonal Antisera and Monoclonal Antibodies

Once obtained from their living hosts, the polyclonal antisera and the monoclonal antibodies were evaluated and verified for their ability to bind specifically with the A and B domains of the ER. The polyclonal antiserum prepared as described herein has been found to bind specifically with the A/B region of human ER in the 8S, 4S, and 5S isoforms. The polyclonal antisera therefore are able to identify the presence of intact A/B regions in the various ER states—be they the unactivated 8S form; the activated but untransformed 4S form; or the activated and transformed 5S form. When utilized within the assay procedures for this purpose, these polyclonal antisera will accurately detect the presence of the A/B region with the ER intracellularly; and will additionally provide the background by which to identify the functional status of the detected ER protein.

In comparison, as empirically demonstrated hereinafter, monoclonal antibodies raised in the described manner are epitope-specific binding antibodies; and thus will bind with the activated human ER in the transformed or untransformed states. This corresponds to the capability of detecting hER in the 4S and the 5S forms only. These monoclonal antibodies are site-specific in their properties; and they will not and do not bind to the unactivated and untransformed 8S form of hER. Accordingly, the monoclonal antibodies will service to identify both the functional "activated but untransformed" as well as the "activated and transformed" state of the ER protein actually present within the cells or tissues being empirically evaluated.

Finally, when the polyclonal antisera and the monoclonal antibodies are employed within immunoassays to determine the presence of ER within a cellular sample, a direct comparison of the empirical results obtained using polyclonal antisera and monoclonal antibodies provides a direct and unequivocal measure of the functional status and activated/transformed state of the ER protein being empirically detected.

Moreover, the ability to identify not only the functional status but also the activation and transformation states of human estrogen receptor in a cellular sample thus allows the use of assay procedures for the accurate quantitation of cytosolic estrogen receptors in breast cancer tissue samples. By employing the polyclonal antisera and the monoclonal antibodies within individual assays, the resulting data can be used to correlate not only the mere presence of estrogen receptor but also the quantity of function in the receptor within the tissue obtained from a single source or patient. On this basis, it now becomes possible to segregate breast cancer patients more accurately into two populations: those who are likely to respond to hormonal therapy via the presence of an intact and functional estrogen receptor; and those who are not likely to respond to hormones despite the presence of estrogen receptors because these are either not intact and/or non-functional.

PREFERRED TEST PROTOCOLS

To demonstrate the uses of the polyclonal antisera and the monoclonal antibodies for such assay purposes, a set of preferred protocols are provided which will illustrate the range of methods and manipulative steps able to be employed in the performance and the utilization of immunoassays. It will be expressly understood however, that the procedural steps described hereinafter are merely representative of the nature and manipulative steps employed within immunoassays generally. The described protocols are not self-limiting and are not restrictive to only the described manipulative steps and the test conditions employed. To the contrary, it is deemed and expected that a wide variety of homogeneous and heterogeneous immunoassay systems may be employed; that the parameters of concentration, volume, temperature, and choice of reagents can be varied extensively at will; that the identifying labels used with the polyclonal antisera and the monoclonal antibodies in such assays may be either isotopic or non-isotopic in nature; and that the protocols might be embodied as kits or other test apparatus in commercially salable form rather than individually prepared reagents and reactants. The present invention presumes and incorporates by reference any conventionally known immunoassay techniques, procedures, protocols, substrates, and other non-decisive factors and parameters— all of which may be usefully employed within any given immunoassay procedure. None of these are deemed to be essential or dominant criteria when performing the methods of the present invention.

Accordingly, for illustrative purposes only, preferred protocols utilizing polyclonal antisera and monoclonal antibodies specific against at least one epitope in the A/B domains of human estrogen receptor are given hereinafter.

A. Estrogen Receptor Assay Protocol

Buffers

TEGM buffer consists of 10 mM Tris-HCl; 1 mM ethylenediamine tetracetic acid (EDTA); 10% vol/vol glycerol; 10 mM sodium molybdate; 10 mM monothioglycerol; and 0.02% sodium azide (pH 7.4 at 2° C.).

Preparation Of Cytosol Fractions

The tissue sample is pulverized, weighed, and placed in a test tube on ice. Unless otherwise stated, all manipulations are carried out at 0°–4° C. Ice cold TEGM buffer is added to the tissue in a 4:1 vol/wt and homogenized with a polytron Pt-10 using 5 sec. bursts and 30 sec. cooling periods in between bursts. The homogenate is then transferred into ultracentrifuge tubes; and the homogenate is centrifuged at 100,000×gravity for 45 minutes to obtain the high speed supernatant of cytosol. The cytosol is transferred to a clean tube and placed on ice.

Preparation Of Radioactive Estradiol Stock Solutions

[$^3$H] estradiol is obtained in solution of benzene/ethanol. Aliquot is removed and dried under nitrogen. The dried material is resuspended in a small volume (2–5 ul) of ethanol; buffer is then added to dissolve the radiolabeled estradiol. The concentration of the estradiol [$E_2$] is then determined by conventional radioactive counting.

Incubation Of The Cytosol With Radiolabeled Estradiol

Aliquots of the cytosol are then incubated with 5 nM of radiolabeled estradiol at 0° C. for 16 hours to form the estrogen receptor/estradiol complexes. To determine the nonspecific binding, parallel aliquots of cytosol were incubated with [$^3$H]$E_2$ and a 100 fold molar excess of unlabeled diethylstilbestrol.

Removal Of Free Radioactive Estradiol With Dextran Coated Charcoal "DCC"

The DCC suspension in TEGM buffer is centrifuged and the supernatant is discarded. The cytosol incubation is then transferred into the DCC pellet and mixed and kept on ice for 20 minutes with intermittent mixing. The suspension is then centrifuged at 1,000×g (gravity) for 10 minutes and the supernatant is used as a source of labeled cytosol.

B. Determination Of Estrogen Receptors By An Enzyme Immunoassay 96-well Microtiter plates are preferably used. Aliquots of bovine serum albumin conjugated oligopeptide in 50 ul of phosphate buffered saline (3 ug/50 ul) are pipetted into each well and allowed to bind at 0° C. for 16 hours. The wells are then coated with 200 ul of 2% bovine serum albumin (BSA) in phosphate buffered saline (PBS) for 1–2 hours at 25° C. The plates are then washed with PBS three times and used for competitive binding assay.

An aliquot of the desired antibody, either monoclonal or polyclonal, is diluted 1:2,000 with BSA/PBS and 50 ul are incubated for 16 hours at 0°–2° C. with increasing volumes of the human breast tissue cytosol (10–200 ul). This allows the antibody receptor interaction to form the antigen-antibody complex. The (polyclonal or monoclonal) antibody/cytosol mixture is then added to the wells of the microtiter plate and incubated at 0°–2° C. for an additional 16 hours. The individual wells are then washed three times with PBS; and a secondary antibody previously conjugated to alkaline phosphatase is added in 1:5,000 dilution in BSA/PBS to each well and the reaction mixture incubated at 25° C. for 2 hours. The unbound (polyclonal or monoclonal) antibody is then removed and the wells washed three times in PBS. An enzyme substrate for alkaline phosphatase is then added to each well and incubated at 25° C. for 30 minutes in the dark. The color reaction is then stopped by addition of 0.5N NaOH. The color product of the reaction is measured by ELISA microtiter reading at 450 nm.

Control incubations are made in the absence of cytosol. This allows measurement of all the antibody bound in the reaction mixtures. Nonspecific binding is determined by omitting the primary (polyclonal or monoclonal) antibody. Additional controls are provided by wells that were coated with BSA only and do not contain any oligopeptide. Calf uterine cytosol with known estrogen receptor content is used as external standard to evaluate the reproducibility of the assay.

C. Determination Of The Functionality Of Human Estrogen Receptor

An aliquot of the cytosol to be tested is labeled with radioactive estradiol as described above and is incubated with 25 ug of the antibody at 0°–2° C. for 4–16 hours in the presence of 0.4M KCl. The total sample is then layered together with $^{14}$C-labeled BSA and human gamma-globulin using a 5–20% sucrose density gradient (made in TEGM buffer containing 0.4M KCl, in 4 ml polyallomer ultracentrifuge tubes). The gradients are centrifuged at 50,000 rpm in an SW60 Beckman rotor for 18 hours at 2° C. The gradients are then fractioned into 0.1 ml individual fractions, 0.5 ml of water and 4 ml of Liquiscint are then added and the samples counted for radioactivity. The intact estrogen receptor binds to the antibody and sediments in the 7–8 S region of the gradient. Estrogen receptors with defective, missing, or altered domains will not interact with antibody and therefore will sediment in the 4–5 S region.

D. Binding Of (Polyclonal Or Monoclonal) Anti-ER Antibodies To ER

Sources of Tissue

Human breast cancer tissue was obtained through the Steroid Receptor Assay Laboratory of Boston University. Tissue procurement was performed as described in Muller et al., *Cancer Res.* 40:2941 (1980). Calf uterine tissue was obtained from a local slaughter house as described previously [Traish et al. , *Endocrinology* 118:1327 (1986)]. Rat uterine tissue was obtained from 21–23 day old female Sprague-Dawley CD rats. Rat prostates were obtained from mature 24 h castrated males (Charles River Breeding Laboratories).

Cytosol fractions from each kind of tissue were prepared in TT buffer as described previously [Traish et al., *Endocrinology* 118:1327 (1986)]. Briefly, fresh tissue or frozen tissue powder was homogenized (1 g/4 ml) in buffer TT, pH 7.4 at 2° C. The homogenate was then centrifuged at 105,000×g for 45 min. at 2° C. and the supernatant fraction (cytosol) was used for receptor binding studies.

Labeling Of Cytosols With Steroid Hormones

To label the ER, aliquots of the tissue cytosols were incubated at 2° C. for 4 h with 5 nM [$^3$H]E$_2$ in the absence (total binding) or presence (non-specific binding) of a 100 fold molar excess of unlabeled DES. Progesterone receptors were labeled by incubating calf uterine cytosol with 15 nM [$^3$H]ORG2058 in the absence or presence of unlabeled ORG2058 as described previously [Traish et al., *Steroids* 47:157 (1986)]. Androgen receptors were labeled by incubating rat prostatic cytosol with 10 nM [$^3$H]DMNT in the absence or presence of unlabeled DHT. Glucocorticoid receptors were labeled by incubating calf uterine cytosol with 10 nM [$^3$H]TA and 20 nM unlabeled ORG2058 in the absence or presence of unlabeled TA as described previously. At the end of the incubation, free radioactivity was removed with DCC pellets and the supernatant used for antibody-receptor interactions.

Sucrose Density Gradient Analysis

Sucrose density gradients (8–30%) were prepared in TT buffer containing 0.4M KCl. In some experiments (as indicated) the gradients were made 8–30% in TT buffer containing 10% glycerol with or without 0.4M KCl. Samples to be analyzed were layered on the gradient together with $^{14}$C-labeled sedimentation markers. The gradients were centrifuged at 50,000 rpm in an SW60 rotor for 18 h at °C. Gradients were fractioned into individual 0.1 ml fractions, scintillation fluid was added, and radioactivity counted.

To further document and demonstrate the individual parts of the present invention and the major advantages and abilities provided by the invention as a whole, a variety of different experiments were performed and the resulting data recorded. These empirical experiments and data are provided hereinafter in order that the properties, characteristics, uses, and advantages of each component part may be properly appreciated and understood. It will be recalled, however, that these experiments are directed to estrogen receptor; and that the specific embodiments, procedures, modes of preparation, and immunoassays performed are merely illustrative and representative of the totality of embodiments encompassed within the scope of the present invention.

II. ANTIBODIES SPECIFIC FOR AT LEAST ONE EPITOPE WITHIN THE A/B REGION OF hER

A. Preparation Of Synthetic Oligopeptides And Immunogens Representative Of The A/B Domains Within Human Estrogen Receptor Protein The A/B region of human estrogen receptor (hER) is encompassed by the amino acids at about positions 1–184 in the native protein. FIG. 1 and FIG. 1A depict the amino acid sequence of the transactivation A and B domains and of the three oligopeptides chosen as haptens and immunogens to obtain specific monoclonal antibodies and polyclonal antisera. It will be noted that:

Peptide NMT-1 represents the segment of amino acid residues from positions 140–154 within native hER as:

(140) Thr-Val-Arg-G17-Ala-Gly-Pro-Pro-Ala-Phe-Tyr-Arg-Pro-Asn-Ser (154).

Peptide NMT-2 represents the segment of amino acid residues from positions 155–169 within native hER as:

(155) Asp-Asn-Arg-Gln-Gly-Gly-Arg-Glu-Arg-Leu-Ala-Ser-Thr-Asn (169).

Peptide NMT-3 represents the segment of amino acid residues from positions 170–184 of the native hER:

(170) Asp-Lys-Gly-Ser-Met-Ala-Met-Glu-Ser-Ala-Lys-Glu-Thr-Arg-Tyr (184).

Cumulatively, therefore, the three peptide sequences are identical to about 22% of the total A/B domains of human ER. The conserved cystein residues believed to play a role in the tertiary structure of the putative zinc-binding fingers are noted by asterisks within FIG. 1.

Synthesis Of Oligopeptides

The oligopeptides NMT-1, NMT-2 and NMT-3 were prepared using conventionally known solid phase peptide synthesis methods [Merrifield, R. B., *J. Am. Chem. Soc.* 85:2149 (1963)]. Once synthesized, the individual oligopeptides were purified by gel filtration and analyzed for purity by HPLC. Analysis of the amino acid composition correlated well with the primary sequence. Each peptide contained one [$^3$H]-labeled amino acid as a tracer. This provided the means for determining the efficiency of coupling to the various carrier proteins.

Immunization Of Mice

Groups (four animals/group) of female mice [(BALB/cA/J) F$_1$] 6–8 weeks old were also immunized by injecting s.c. 100 ug of the designated oligopeptides, emulsified in Freund's complete adjuvant. Two s.c. booster injections were given at 3 week intervals. The mice were bled through the vein and the sera were tested for antibodies by sucrose density gradient analysis. Those mice which appeared to have antibodies against ER were then selected.

Polyclonal Antisera Production

The immunogen and the raising of antisera did show some variation among the host animals (6 mice per group).

Positive polyclonal antisera, as determined by sucrose density gradient analysis were obtained against all peptides, however, the response rate was different for each peptide used as an immunogen. While all mice (6 per group) immunized with either peptides NMT-1 or NMT-2 produced positive polyclonal antisera, only two positive antisera were obtained against peptide NMT-3 from the animals employed.

Within this detailed description, the individual peptide specific polyclonal antisera obtained against peptide NMT-1 will be referred to as poly-1 (A-D) since each antiserum was individually obtained from only one rabbit and was never mixed with any other antiserum. Similarly, polyclonal antisera raised against peptide NMT-2 will be identified as poly-2 (A-D) respectively; and polyclonal antisera specific for peptide NMT-3 are individually designated as poly-3 (A-D). The properties, specificity, titer, and other characteristics of the polyclonal antisera were then empirically evaluated.

B. Properties And Characteristics Of Anti-A/B Domain Human ER Polyclonal Antisera

Experimental Series 1

Interactions Of Anti-A/B Domain Mouse Polyclonal Antisera With 8S hER

In cell free systems the solubilized ER can be found as 8S complexes (unactivated, untransformed), 4S complexes (activated but untransformed), or 5S complexes (activated and transformed). To test if the native 8S receptor complex will bind with anti-A/B domain antibodies, cytosol was incubated with [$^3$H]E$_2$ in absence or presence of unlabeled DES as described previously herein. After removal of free steroids with DCC, samples were incubated with each polyclonal antiserum for 4 h at 0° C. and then analyzed on sucrose density gradients prepared in low salt buffer.

Interaction Of The Polyclonal Antisera With The 4S and 5S hER

To evaluate further the binding of these polyclonal antibodies, the binding of the antisera to the activated (4S) and transformed (5S) receptor complexes was then examined.

Calf uterine was prepared in TGT buffer without molybdate. The cytosol was incubated at 0° C. for 90 min with 5 nM [$^3$H]E$_2$ in absence or presence of unlabeled DES. Samples were then incubated at 28° C. for 30 min to induce heat transformations of ER. The samples were placed on ice and free steroids were removed with DCC. Aliquots of these incubations were then mixed with the indicated antisera and kept at 0°–4° C. for 4 h. Samples were then analyzed on sucrose density gradients containing 0.4M KCl.

Results

Polyclonal antisera raised against NMT-1, (spanning amino acids 140–154) recognized some forms of the ER and an ER-related 55 kDa protein present only in nuclear extracts of estrogen-target tissues. Polyclonal antisera raised against NMT-2 (spanning amino acids 155–169) and NMT-3 (spanning amino acids 170–184) individually reacted with some forms of ER receptor as shown by sucrose density gradients and immunoprecipitation, but not by western blot analysis. The antisera bound the unactivated (8S) ER, the salt-activated (4S), and heat transformed (5S) ER complexes. All antisera were found to be site-specific since binding of salt-activated ER to the antisera was inhibited by preincubation of the antisera with 50 ug/ml of free synthetic peptide. These results are summarized by Table 1 below.

TABLE 1

Reactivity of Polyclonal Antisera

| Polyclonal Antiserum | Animal Producing Positive Antiserum | Raised Against hER Oligopeptide (Position Nos.) | Form of hER Detected | | |
|---|---|---|---|---|---|
| | | | Unactivated (8S) | Salt-Activated (4S) | Heat-Transformed (5S) |
| poly-1 (A-D) | 4 of 4 | NMT-1 (Nos. 140–154) | Yes | Yes | Yes |
| poly-2 (A-D) | 4 of 4 | NMT-2 (Nos. 155–169) | Yes | Yes | Yes |
| poly-3 (A-D) | 1 of 4 | NMT-3 (Nos. 170–184) | Yes | Yes | Yes |

Experimental Series 2

Lack Of Species Specificity Of Anti-A/B Domain Mouse Polyclonal Antisera Raised Against hER Since the A/B Domain of oligopeptides were synthesized according to the published amino acids residue sequence of the human ER, it was important to determine the binding specificity of these antisera. Accordingly, tissue cytosols (5–7 mg protein/ml) from human breast cancer, calf uterus, and rat uterus were prepared and labeled with [$^3$H]E$_2$ as described previously herein. Aliquots of the DCC-treated cytosol were then reincubated at 0° C. for 4 h with the three polyclonal antisera. Samples were then analyzed on sucrose density gradients. The results are given by Table 2 below.

Table 2 summarizes the overall results of incubation of [$^3$H]E2-labeled ER from calf uterine cytosols, and rat uterine cytosols, and human breast cancer tissue cytosols with the three polyclonal antisera. All three antisera recognized and bound to ER from the various animal species, albeit, with less affinity for the rat uterine ER. Clearly there is an absence of species specificity for these anti-A/B domain antisera.

TABLE 2

Reaction With Differing Cytosols of ER:

| Polyclonal Antisera | Human Breast Cancer | Rat Uterus | Calf Uterus |
|---|---|---|---|
| poly-1 (A-D) | Yes | Yes | Yes |
| poly-2 (A-D) | Yes | Yes | Yes |
| poly-3 (A-D) | Yes | Yes | Yes |

This lack of species specificity for the A/B domain is also shown by FIGS. 2–4 respectively—which demonstrate the absence of specificity for anti-(NMT-1 ), anti (NMT-2), and anti-(NMT-3) mouse polyclonal antisera individually.

FIGS. 2A–2D illustrate the binding of four different anti-NMT-1 mouse polyclonal antisera to estrogen receptor in calf uteri (CU-ER). Calf uterine cytosol was prepared in buffer TEGT and labeled with 10 nM [$^3$H]ER for 2 hours at 0° C. either with or without unlabeled DES to determine the nonspecific binding. At the end of the incubation, samples were treated with DCC at 0° C. for 30 min. After centrifugation, aliquots of the supernatant (200 ul) were further incubated with the preimmune sera (open circles) as a control or with one of four individual antisera (closed circles) for 4 hours at 0° C. and then analyzed on SDG/0.4M KCl. Each of FIGS. 2A–2D represents a different anti-NMT-1 antiserum.

Similarly, FIGS. 3A–3D illustrate the binding of four different anti-NMT-2 mouse polyclonal antisera to Cu-ER. Experimental conditions and protocols are identical to those for FIG. 2. FIGS. 3A–3D represent the antisera of four individually immunized mice. Arrows represent the ovalbumin marker.

Finally, FIGS. 4A–4D illustrate the binding of four different anti-NMT-3 mouse polyclonal antisera to CU-ER. Experimental conditions and protocols are identical to those for FIGS. 2 and 3. FIGS. 4A–4D represent the antisera of four different immunized mice. Arrows represent the ovalbumin marker.

C. Anti-A/B Domain Specific Monoclonal Antibodies

The Choice Of Mouse Antisera Prepared Against Oligopeptide NMT-1

The polyclonal antibodies to peptide NMT-1 were shown to cross-react with a nuclear protein that was present mainly in ER+ breast tumors. For this reason, monoclonals to peptide NMT-1 were obtained. five clones were isolated but only two were characterized, NMT-1-C6 and NMT-1-E7. These were characterized with respect to their ability to recognize the native ER.

Experimental Series 3

ELISA Assay Of Monoclonal Antibodies Prepared Against Peptide NMT-1

After cell fusion, the tissue culture supernatants from the various clones were initially screened for monoclonal antibodies (MAb) against oligopeptide NMT-1 conjugated to BSA. Fifteen clones appeared to contain MAbs against this oligopeptide. To determine if the clones secreted immunoglobulins against the oligopeptide, the spent tissue culture medium from each clone was assayed by ELISA for presence of antibodies. The assay was performed as follows.

Aliquots (50 ul) of the bovine serum albumin conjugated peptide (3 ug) in PBS were dispersed into the microtiter wells and incubated at 0°–4° C. for 16–20 h. The plates were then blocked with 2% BSA in PBS and used to screen the tissue culture supernatants from the various hybridoma clones. Tissue culture supernatants of various dilutions from fusion No. 1 or fusion No. 2 were added to microtiter plates in a final volume of 50 ul and incubated at 0°14 4° C. for 16 h. The plates were then washed and the antibody binding activity was determined by alkaline-phosphatase activity conjugated to rabbit antimouse antibody. Mouse polyclonal antiserum against polypeptide NMT-1 was used as a control (IMS).

Analysis Of Estrogen Receptor Interaction With Monoclonal Antibodies Produced Against Oligopeptide NMT-1 By Sucrose Density Gradients Calf uterine cytosol was prepared in buffer TGET/MO and labeled with 10 nM [$^3$H]E$_2$ at 0° C. for 4 h. To determine non-specific binding, aliquots were labeled with [$^3$H]E$_2$ in the presence of 5 uM unlabeled DES. At the end of the incubation, free radioactivity was removed with dextran-coated charcoal pellets and samples were removed and placed in polypropylene microfuge tubes. Aliquots (50–100 ug equivalent of the antibody) of the ascites fluid from the various clones were then added and the samples were reincubated at 0° C. for 16 h. Additional samples were treated either with an equimixture of ascites from four clones or remained untreated (control). Samples were then analyzed on 5–20% sucrose density gradients made in TGET/MO buffer containing 0.4M KCl as described in the methods.

Results

Five monoclonal antibodies were developed against peptide NMT-1 (amino acids 140–154 of hER). These monoclonal antibodies were found to be receptor-specific and exhibited all the characteristics described for the polyclonal antisera raised against this peptide. Western blot analysis demonstrated that each of the five monoclonal antibodies recognized a 55 kDa protein extracted from nuclei of estrogen target tissues and from human breast tissue samples that were shown to contain cytoplasmic estrogen receptor by ligand binding assays. The monoclonal antibodies recognize the estrogen receptor in immunocytochemical assay using human breast tissue and in rat uterine tissue. The monoclonal antibodies to NMT-1 also detect a nuclear protein in the MCF-7 cell line (human breast cancer cell line).

Experimental Series 5

Interaction Of anti-A/B Domain Monoclonal Antibodies Prepared Against Oligopeptide NMT-1 With [[$^3$H]E$_2$ From Various Mammalian Species Several studies have suggested that ER protein has two conserved regions, namely the DNA-binding (region "C") and the general steroid binding domain (region "E"). Thus, it is possible that the MAbs produced against the A/B transactivation domains of hER will also interact with ER from various species. To empirically demonstrate such interaction, cytosols from human breast cancer tissue, calf uteri and rat uteri were labeled with [$^3$H]E$_2$ for 16 h at 0° C. After removal of free radioactivity with DCC, samples were incubated without (control) or with monoclonal antibodies NMT-1-C6 and NMT-1-E7. After 16 h at 0° C. the samples were analyzed by sucrose density gradients as described earlier. The overall results are summarized by Table 3.

Receptor Specificity Of Anti-A/B Domain Monoclonal Antibodies

It has been suggested that the DNA binding domain of receptor proteins in the steroid hormone family share 42–95% homology with each other [Evans, R. M., Science 240:889 (1988)]. The production of MAbs to this A and B region of human ER thus might result in MAbs which cross-react with progesterone receptor, glucocorticoid receptor, and androgen receptor. The experiment was conducted to test this possibility.

Initially, progesterone receptors of calf uterine cytosol were labeled with [$^3$H]ORG2058; glucocorticoid receptors were labeled by incubating calf uterine cytosol with [$^3$H] dexamethasone; and androgen receptors of rat ventral prostate cytosol were labeled with [$^3$H] DMNT as follows.

Cytosol fractions from each tissue were prepared in the appropriate buffer, as described previously. Briefly, fresh tissue or frozen tissue powder was homogenized (1 g/4 ml) in buffer TT, pH 7.4 at 2° C. The homogenate was then centrifuged at 105,000×g for 45 min at 2° C. and the supernatant fraction (cytosol) was used for receptor binding studies.

To label the ER aliquots of the calf or human breast tissue, cytosols were incubated at 2° C. for 4 h with 5 nM [$^3$H]E$_2$ in the absence (total binding) or presence (non-specific binding) of a 100 fold molar excess of unlabeled DES as previously reported [Muller et al. *J. Bio. Chem.* 258:9227–9236 (1983); Muller et al., *Cancer Res.* 40:2941 (1980)]. Progesterone receptors were labeled by incubating calf uterine cytosol with 15 nM [$^3$H]ORG2058 in the absence or presence of unlabeled ORG2058 as described previously [Traish et al. *Steroids* 47:157 (1986)]. Androgen receptors were labeled by incubating rat prostate cytosol with 10 nM [$^3$H] DMNT in the absence or presence of unlabeled DHT; and glucocorticoid receptors were labeled by incubating calf uterine cytosol with 10 nM [$^3$H] dexamethasone in the absence or presence of unlabeled DEX as conventionally known [Traish et al. *Endocrinology* 118:1327 (1986)]. At the end of the incubation, free radioactivity was removed with dextran coated charcoal pellets and the supernatant used for antibody-receptor interactions.

Individual aliquots of these labeled receptor preparations were then incubated at 0° C. for 16 h with an aliquot of monoclonal antibody NMT-1-C6 and NMT-1-E7. As a control, other aliquoted samples were incubated with buffer only. All samples were then analyzed on SDG as described previously. The overall results are summarized within Table 3 also.

two antibodies together produced a larger complex than binding of either alone.

Experimental Series 5

Binding Of Monoclonal NMT-1-C6 And NMT-1-E7 To Estrogen Receptor

Figure 5A:
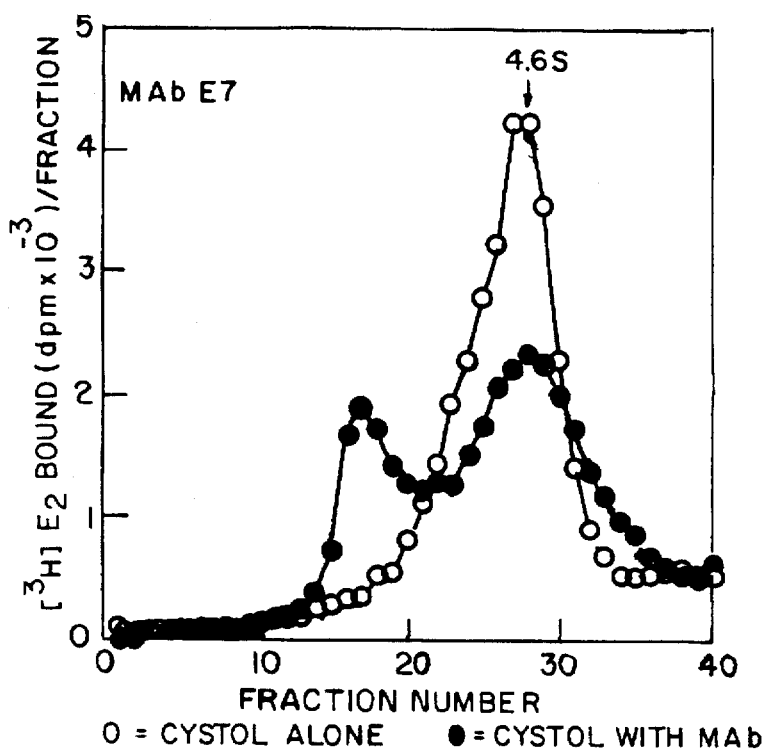
FIGS. 5A–5B are graphs illustrating estrogen receptor interactions in calf uterine cytosol with monoclonal antibodies anti-NMT-1-C6 and anti-NMT-1-E7.
Figure 5B:
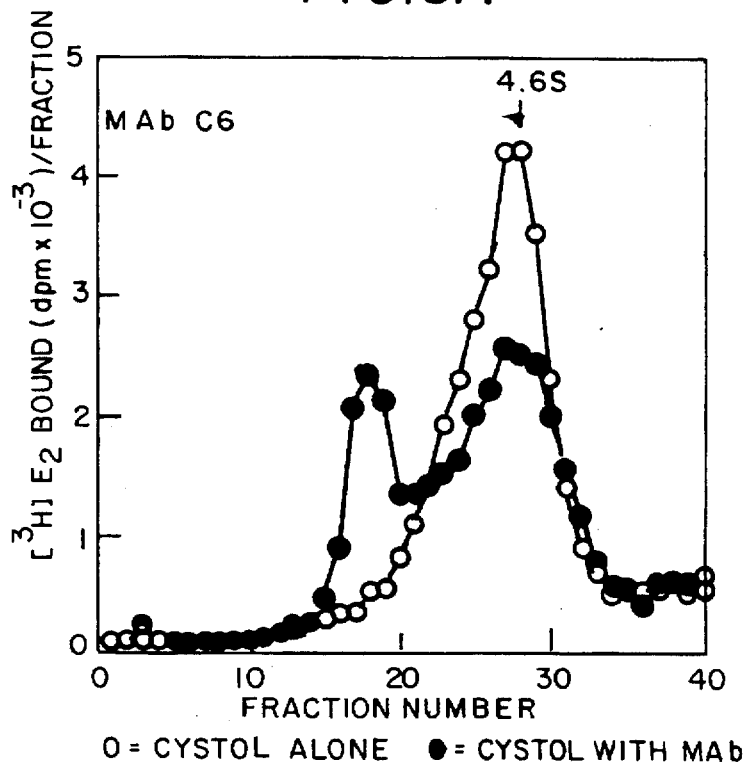

Specifically, FIGS. 5A and 5B illustrate ER interaction with antibody from hybridoma MAb#NMT-1 C6 and E7. Calf uterine cytosol was prepared in buffer TEGT and labeled with 10 nM [$^3$H]E$_2$ at 0° C. for 2 hours. 200 ul of the labeled cytosol were incubated with 200 ul of hybridoma supernatants from clone E7 (FIG. 5A), or C6 (FIG. 5B) for 16 hours at 0° C. 200 ul of buffer was added to the control. Free radioactivity was removed by DCC pellet. Samples were then analyzed on 5–20% SDG/0.4M KCl made in TEGT buffer. The arrows represent sedimentation of the $^{14}$C-labeled human serum albumin. Open circles represent the control while closed circles represent the addition of the monoclonal antibody.

Additional data is provided by Tables 4 and 5 respectively. Table 4 summarizes the immunoprecipitation of [$^3$H]E$_2$-ER complex by hybridoma MAb#NMT-1 E7 and C6. Calf uterine cytosol was prepared and labeled as described above, but instead of analyzing the incubations on SDG, protein G was added and incubated with the mixture for 16 hours with agitation of 0° C. As described in material and method, the precipitated ER-MAb complex was counted and the percentage precipitated was calculated based on the specific

TABLE 3

| | Reaction With Cytosols Of ER From: | | | | Reaction With Cytosols Of: | | |
|---|---|---|---|---|---|---|---|
| Anti-NMT-1 Monoclonal Antibody | Human Breast Cancer | Mouse Uterine | Calf Uterine | Rat Uterine | Progesterone Receptor | Androgen Receptor | Glucocorticoid Receptor |
| -C6 | Yes | Yes | Yes | Yes | No | No | No |
| -E7 | Yes | Yes | Yes | Yes | No | No | No |

Figure 8A:
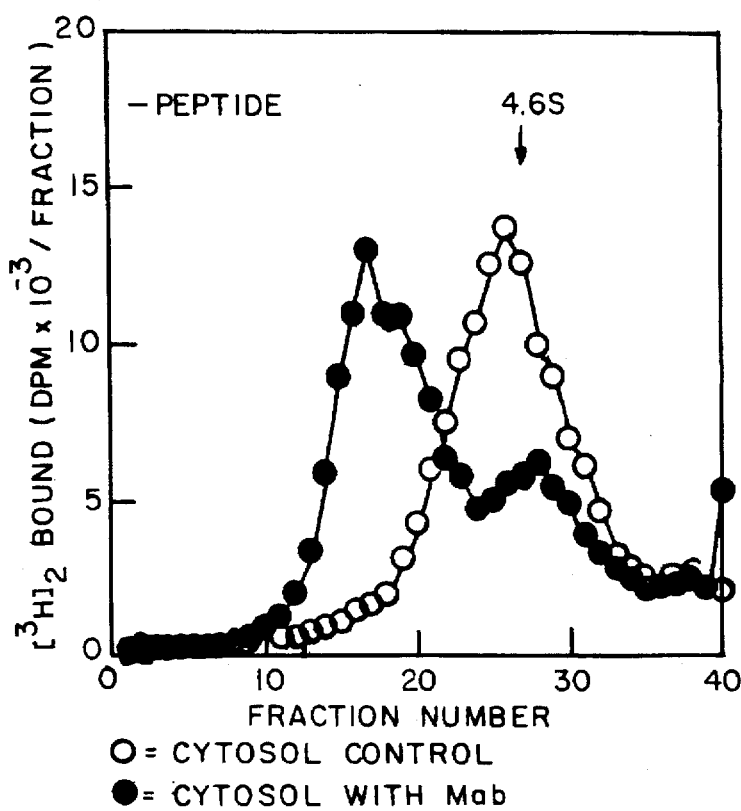
FIGS. 8A–8B are graphs illustrating the site specificity of anti-NMT-1 monoclonal antibodies.
Figure 8B:
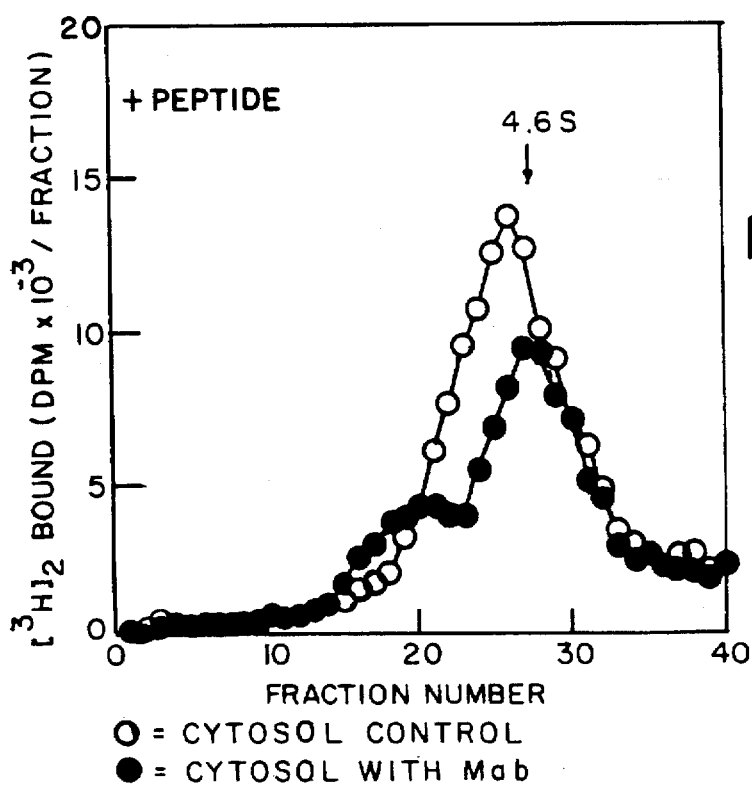
Figure 11:
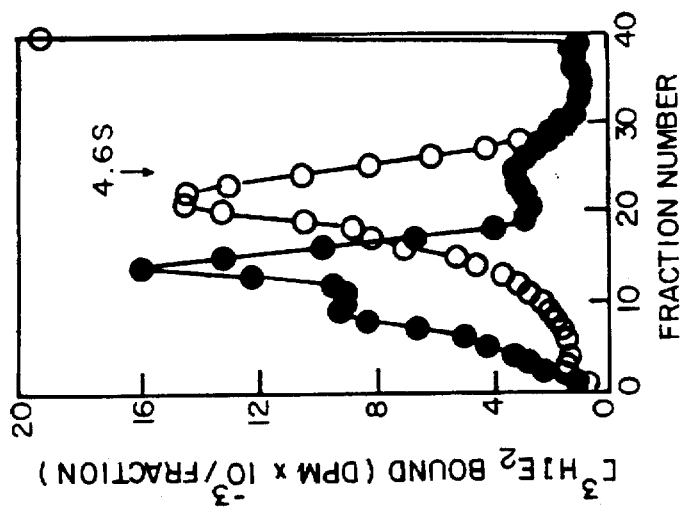
FIG. 11 is a graph illustrating interaction of anti-NMT-1 monoclonal antibodies with heat-transformed 5S estrogen receptor.
Figure 10:
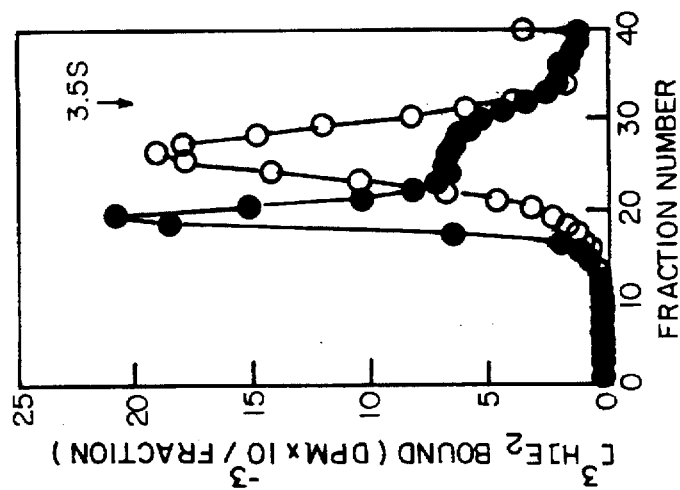
FIG. 10 is a graph illustrating interaction of anti-NMT-1 monoclonal antibodies with salt-activated 4S estrogen receptor.
Figure 9:
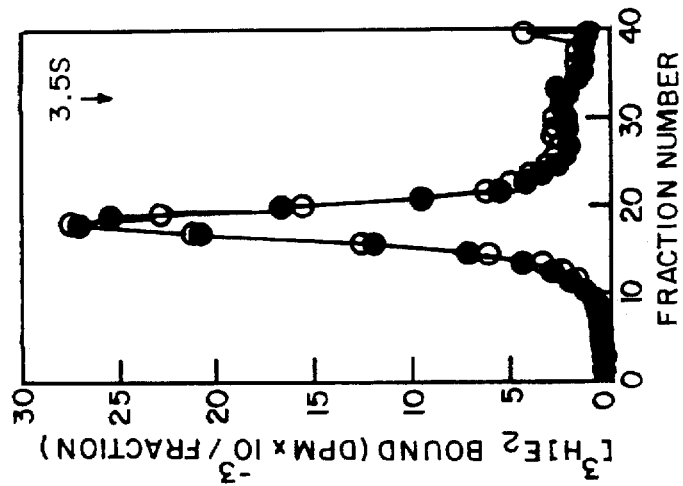
FIG. 9 is a graph illustrating interaction of anti-NMT-1 monoclonal antibodies with molybdate-stabilized, untransformed 8S estrogen receptor.
Figure 12:
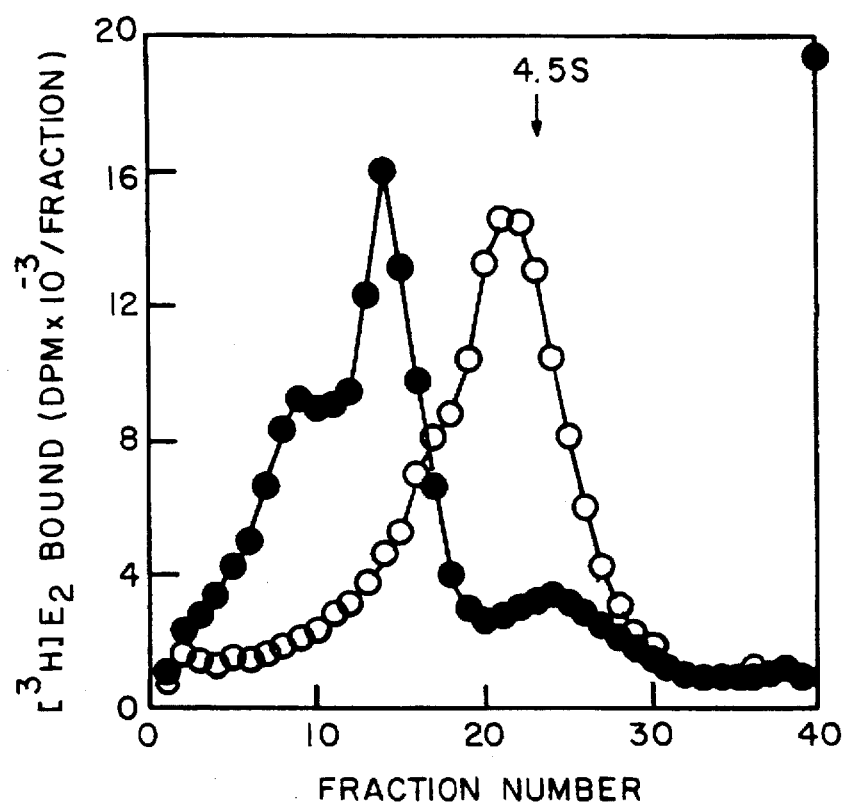
FIG. 12 is a graph illustrating interaction of anti-A/B domain monoclonal antibodies with ammonium sulfate transformed estrogen receptor.
Figure 14A:
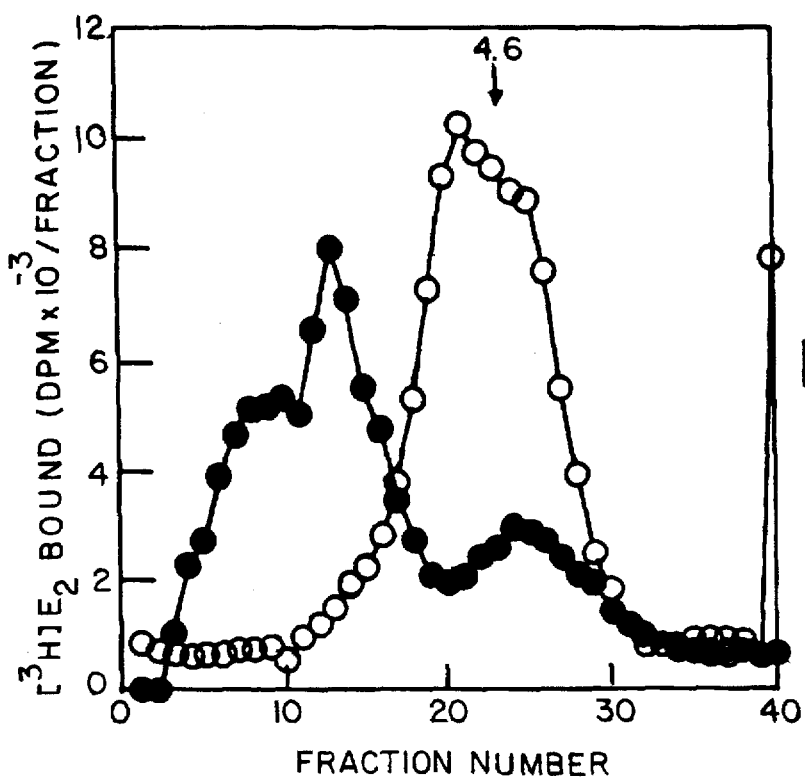
FIGS. 14A–14B are graphs illustrating the non-interference of anti-A/B domain monoclonal antibodies with estrogen receptor transformation.
Figure 14B:
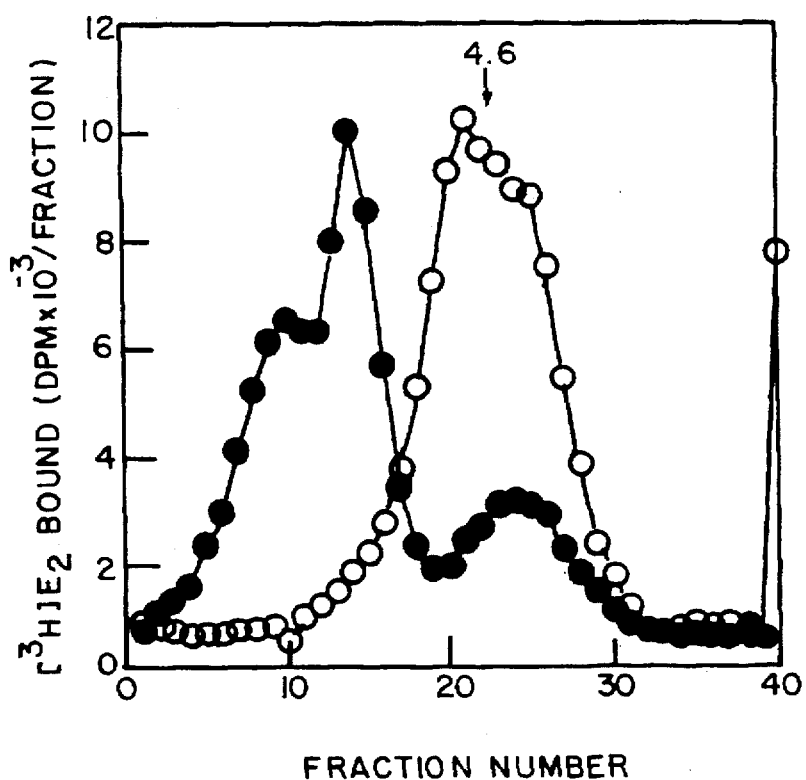
Figure 15:
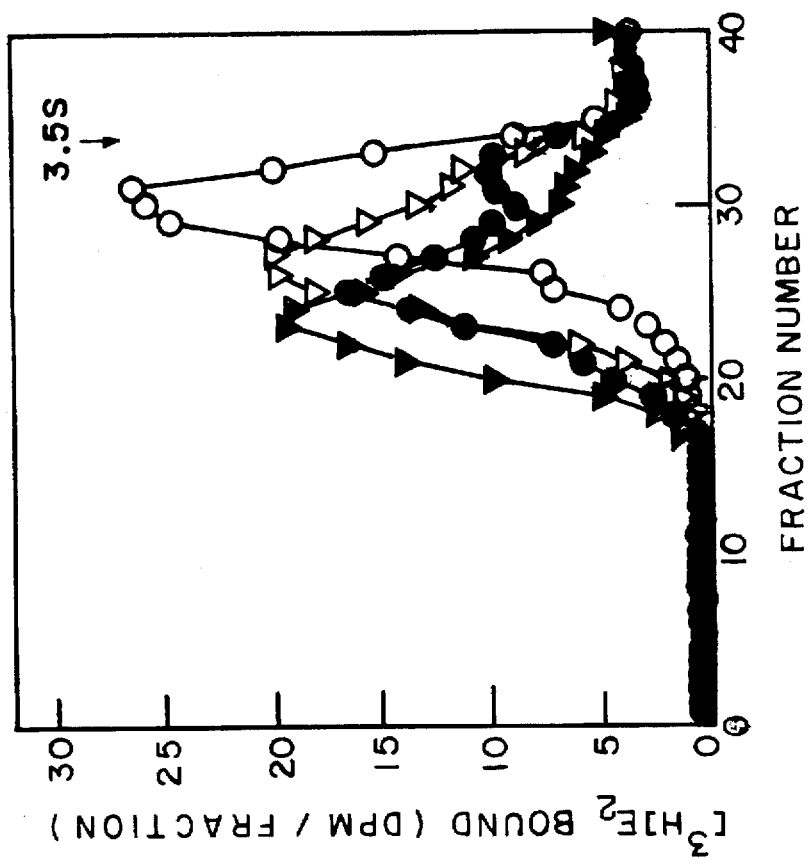
FIG. 15 is a graph illustrating the interactions of different monoclonal antibodies with salt activated estrogen receptor; and, FIGS. 16A, 16B, 16C and 16D are graphs illustrating the binding specificity of anti-A/B monoclonal antibodies using clinical human breast tumor specimens.

A more detailed description of the characteristics of monoclonal antibodies NMT-1-C6 and NMT-1-E7 is presented by FIGS. 5–15 respectively. In brief, FIG. 5 shows the antibodies from the tissue culture media of these two clones. Also these two clones immunoprecipitate ER using the tissue culture supernatants. Ascites were produced from these two clones and were further characterized. FIG. 6 demonstrates that these antibodies are specific for the estrogen receptor. FIG. 7 shows that the antibodies are site specific since displacement of the receptor from the antibody was made in presence of the peptide. FIG. 9 suggests that these antibodies recognize their binding epitope, even the aggregated 8S receptor form. FIG. 10 shows that these antibodies recognize the salt-activated 4S ER form. Heat transformation which results in 5S homodimerization, does not preclude binding of the antibodies; however, heating promotes protease activity and as shown in FIG. 11, only a portion of the receptor is bound to the antibody. FIG. 12 shows that when transformation of the ER is made by ammonium sulfate precipitation, the antibody bound the majority of ER dimer. The proteolyzed receptor generated during heat transformation does not bind to the antibody suggesting that this epitope is in a domain susceptible to degradation (FIG. 13). The binding of the antibody to the 4S does not interfere with dimerization or transformation (FIG. 14). The binding of the antibodies to the A/B region does not interfere with binding o the monoclonal antibody 213 to the DNA-binding domain (FIG. 15). Also, the binding of these binding. Similarly, Table 5 summarizes the immunoprecipitation of [$^3$H]E$_2$-ER complex by MAbs NMT-1 C6 and E7. Samples were prepared the same way as in Table 4 except the MAb used was from the ascites preparations.

TABLE 4

| MAb | [$^3$H]E2ER % Precipitate |
|---|---|
| Buffer | 7% |
| C6 | 23% |
| E7 | 25% |

TABLE 5

| MAb | % [$^3$H]E2-ER Precipitate |
|---|---|
| Buffer | 5% |
| C6 | 66% |
| E7 | 63% |

Figure 6C:
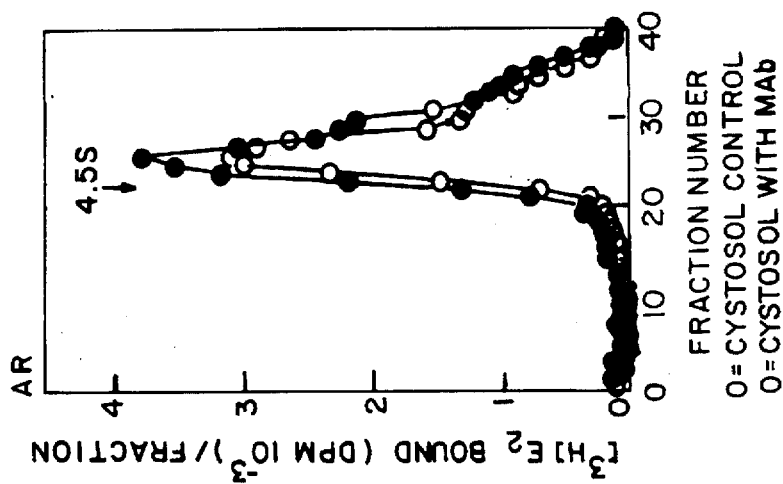
FIGS. 6A, 6B and 6C are graphs illustrating receptor specificity for anti-A/B domain monoclonal antibodies combined with estrogen receptor, progesterone receptor and androgen receptor.
Figure 6B:
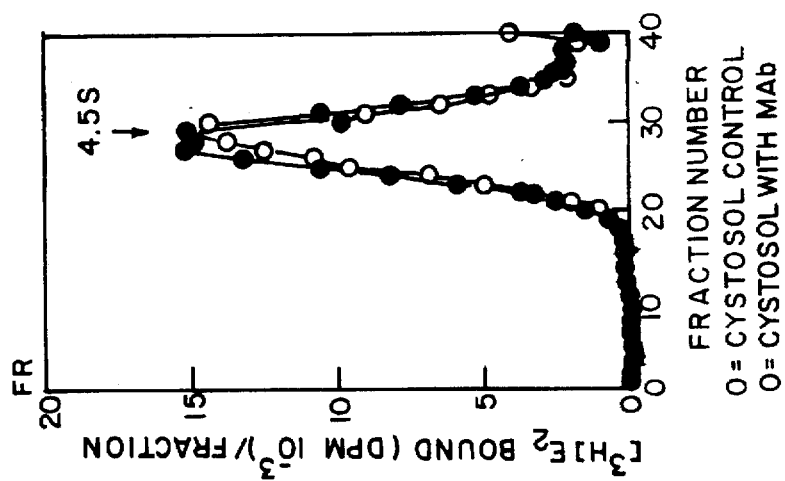
Figure 6A:
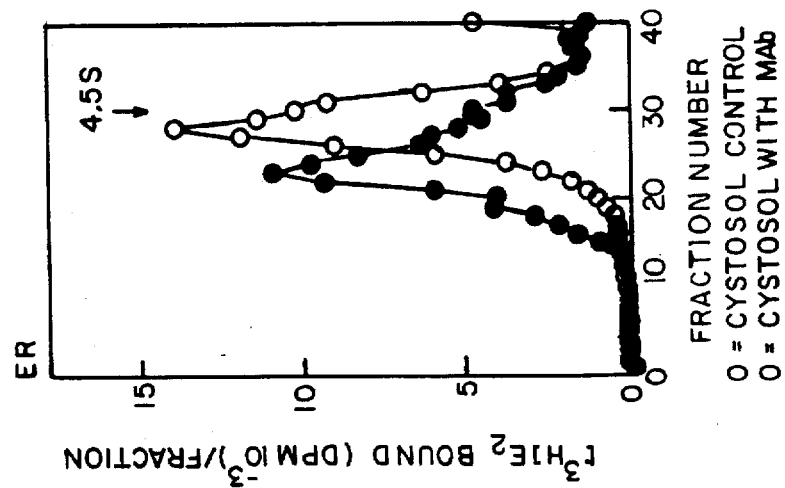

FIGS. 6A–6C illustrate the specificity of the MAbs. Calf uterine cytosol was incubated either with [$^3$H]ORG 2058 or [$^3$H]E$_2$ for 2 hours to label progesterone or estrogen receptors respectively. Rate prostate homogenized in 0.4M KCl, was incubated (as whole tissue extract) with [$^3$H]DMNT to label the androgen receptor. Aliquots of these receptor preparations were then incubated at 0° C. for 16 hours with aliquots of the MAb ascites or with buffer as a control, 0.1 volume 4M KCl was added to all samples, and analyzed on SDG. FIG. 6A represents estrogen receptor; FIG. 6B is progesterone receptor; and FIG. 6C shows androgen receptor. Open circles represent the control; closed circles the MAb; and the arrows represent the bovine serum albumin marker.

In comparison, FIGS. 7A–7C illustrate the absence of species specificity of MAb#NMT-1 as determined by SDG. Cytosols from calf (FIG. 7A) and mouse uteri (FIG. 7B) and human breast cancer tissue (FIG. 7C) were prepared and labeled as described previously herein. Samples were then incubated without monoclonal antibody (open circles) or with monoclonal antibody (closed circles). The incubated samples were analyzed on SDG.

Additional data is provided by Table 6 below. Table 6 summarizes the immunoprecipitation of rat-ER by MAb#NMT-1. Rat uterine tissue was homogenized in 0.4M KCl; centrifuged; and aliquots from the supernatant (whole tissue extract) were incubated in 10 nM [$^3$H]E$_2$ for 16 hours with or without unlabeled DES. Free radioactivity was then removed by DCC. Samples were reincubated for 16 hours with MAb#NMT-1, or buffer, or progesterone receptor monoclonal antibodies as a negative control. Protein G was added next and the mixture incubated with agitation for another 16 hours. To subtract the nonspecific precipitation, Protein G was also added to the DES treated samples.

TABLE 6

| MAb | % Precipitated [$^3$H]E2 |
| --- | --- |
| Buffer | 1% |
| C6 | 38% |
| E7 | 0.6% |

FIGS. 8A and 8B demonstrate the site specificity of MAb#NMT-1 as determined by SDG. Calf uterine cytosol was prepared and labeled as described before. Aliquots of the anti-A/B domain monoclonal antibody were preincubated at 0° C. for 2 hours either in the absence (control) shown by FIG. 9A or the presence shown by FIG. 9B of 50 mg of NMT-1 peptide in TEGT. [$^3$H]E2 labeled cytosol was incubated for 4 hours at 0° C. Each incubation was analyzed on SDG. Closed circles in FIG. 8A represent the sedimentation of [$^3$H]E2 incubated with MAb. Closed circles in FIG. 8B represent the sedimentation of [$^3$H]E2 incubated with MAb bound to peptide. Open circles represent the control with no MAb added.

Experimental Series 6

Binding Of Monoclonal Antibodies To The Untransformed 8S, Activated 4S, and Transformed 5S Isoforms FIG. 9 demonstrates the interaction of MAb#NMT-1-C6 with the molybdate-stabilized untransformed 8S form of ER. Calf uterine cytosol prepared in TEGT buffer containing 10 mM sodium molybdate was incubated at 0° C. for 2 hours with 10 nM [$^3$H]E2 in the absence or presence of unlabeled DES. Free radioactivity was removed by DCC. Aliquots of the cytosol were incubated at 0° C. for 16 hours without (open circles as control) or with 10 ml of monoclonal antibody C6. The samples were analyzed on SDG in buffer without KCl. The arrow represents ovalbumin marker. Experimentals using the E7 monoclonal antibody were substantially similar to the data of FIG. 9. The substantial identity of results between controls and MAb samples shows that the antibody binding site was inaccessible in the native (8S) state of 8 hER.

In comparison, FIG. 10 illustrates the interaction of MAb#NMT-1-C6 with the salt-activated 4S form of ER. Calf uterine cytosol prepared in TEGT was incubated for 2 hours with 10 nM [$^3$H]E2 in the absence or presence of DES. After treatment with DCC, samples were incubated for 16 hours at 0° C. without (open circles as control) or with (closed circles) monoclonal antibody C6. All samples were analyzed on SDG. The results of FIG. 10 show substantial binding of the monoclonal antibody to the 4S form of ER. Experimentals using MAb-E7 were substantially similar to the data of FIG. 10.

Finally, FIG. 11 reveals the interaction of MAb#NMT-1-C6 with the heat-transformed 5S form of ER. Calf uterine cytosol prepared and labeled the same way as previously except that before treating the samples with DCC, they were incubated at 28° C. for 30 min. Aliquots from the labeled-transformed ER were incubated with MAb-C6 in the presence of 0.1 volume of 4M KCl. Open circles represent samples without MAb while closed circles represent samples with MAb. Arrows represent the bovine serum albumin (BSA) marker. The results show substantial binding of the C6 monoclonal antibody to the 5S isoform of ER. Experimental using MAb-E7 shows results substantially similar to the data of FIG. 11.

Experimental Series 7

Other Binding Characteristics of Anti-A/B Domain Monoctonal Antibodies

FIG. 12 shows the interaction of the MAb with the ammonium sulfate transformed ER. Aliquots of the ammonium sulfate transformed ER (as described in Materials and Methods) were incubated with 10 nM [$^3$H]E2 for 2 hours with or without unlabeled DES. After treatment with DCC, samples were incubated for 16 hours with 10 ml of the MAbs (closed circles) or buffer (open circles) in the presence of 0.1 volume KCl. FIG. 12 shows substantial binding of the MAb to the ammonium sulfate transformed ER.

Figure 13A:
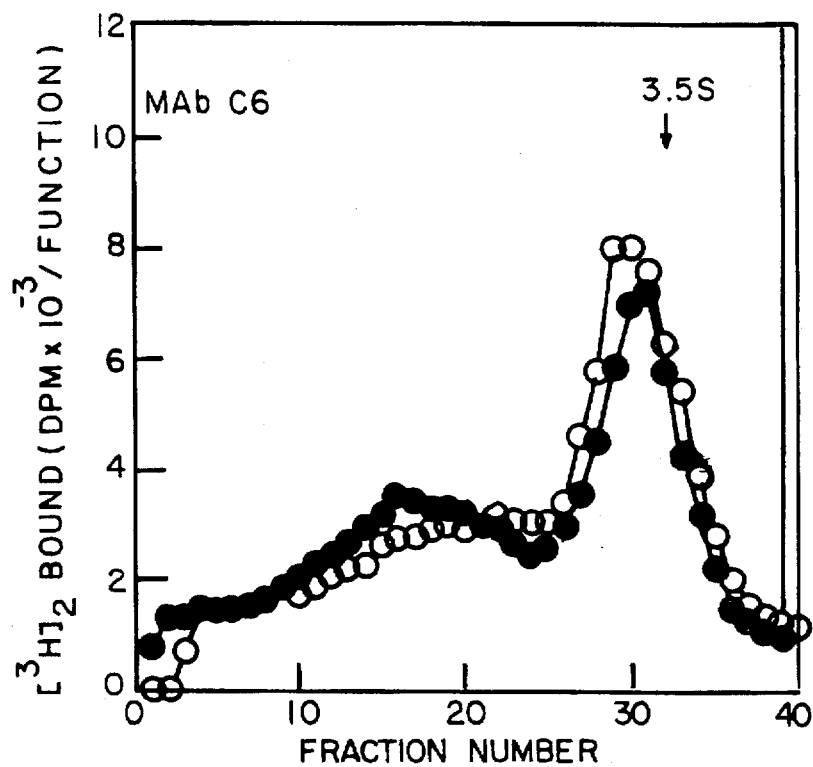
FIGS. 13A–13B are graphs illustrating the aggregation of 5S estrogen receptor in the absence of KCl.
Figure 13B:
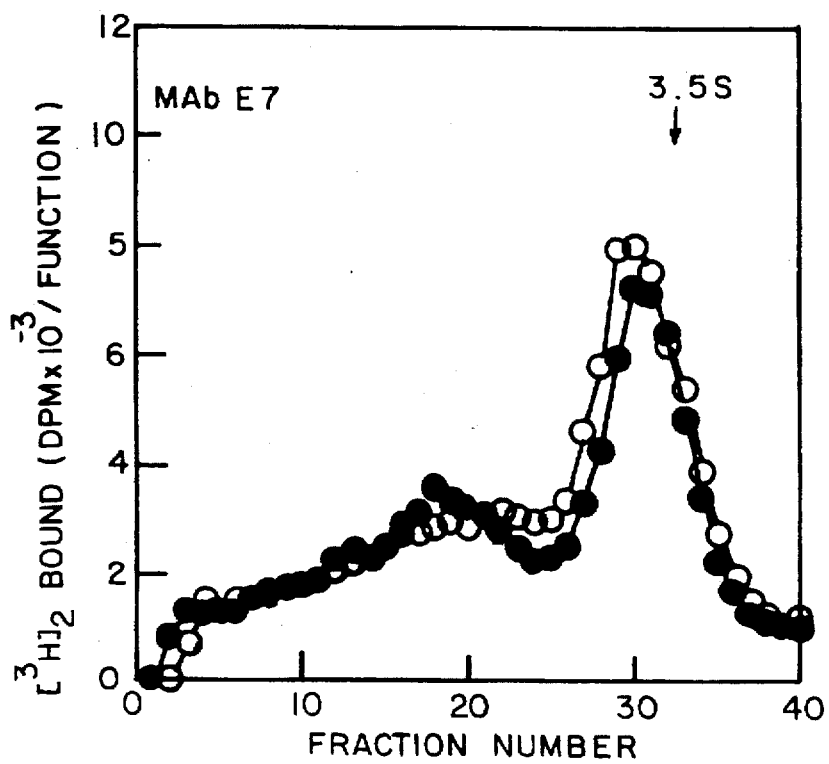

In addition, FIGS. 13A and 13B show the results of adding the MAb-C6 and the MAb-E7 monoclonal antibodies in the aggregation of the 5S ER in the absence of KCl. Calf uterine cytosol was prepared the same way as described previously herein, but no KCl was added either to the samples or to the SDG.

Equally important, the data shown by FIGS. 14A and 14B respectively demonstrate that MAb#NMT-1 does not interfere with receptor transformation. Calf uterine cytosol was prepared and labeled as described herein except that the MAb was added either before heat activating the receptor (FIG. 14A) or after heating (FIG. 14B). Open circles represent that no MAb was added (control) and closed circles show that MAb was added. The arrows indicate the sedimentation of BSA marker.

Lastly, FIG. 15 shows the interaction of both MAb#NMT-1 and MAb#213 (a C-domain specific MAb) with salt activated ER. Calf uterine cytosol prepared and labeled as described in FIG. 9 was aliquoted into 4 samples of 200 ml and incubated for 16 hours at 0° C. with buffer (control open circles), or MAb#NMT-1 (closed circles), or MAb#213 (open triangles), or a mixture of both MAbs (closed triangles). The samples were analyzed on SDG.

D. The Functional Status Of The A/B Domain Of hER As Determined By Anti-A/B Domain Antibodies Experimental Series 8

Figure 16B:
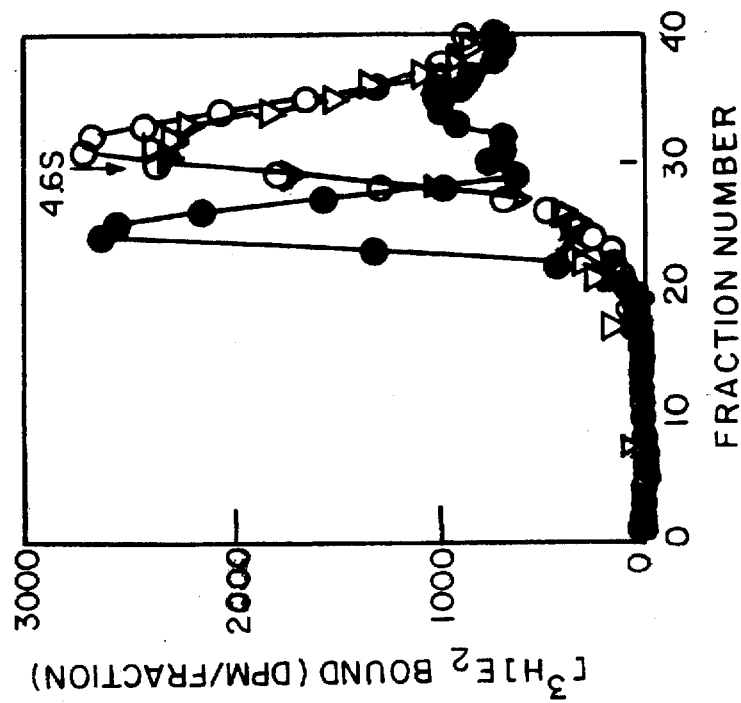
Figure 16A:
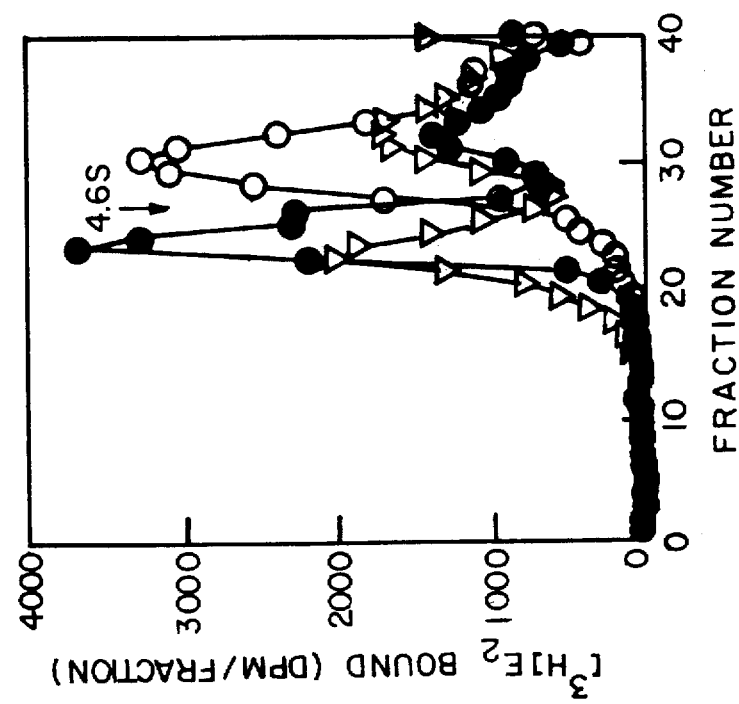
Figure 16D:
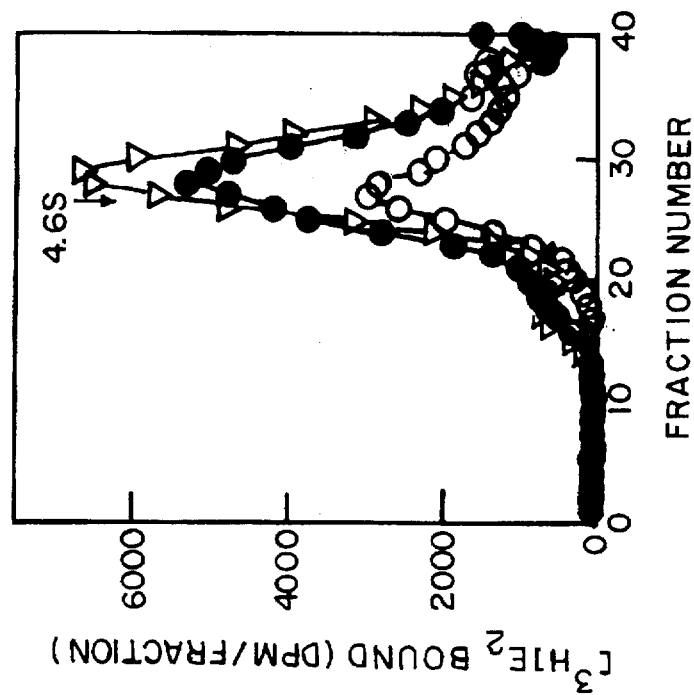
Figure 16C:
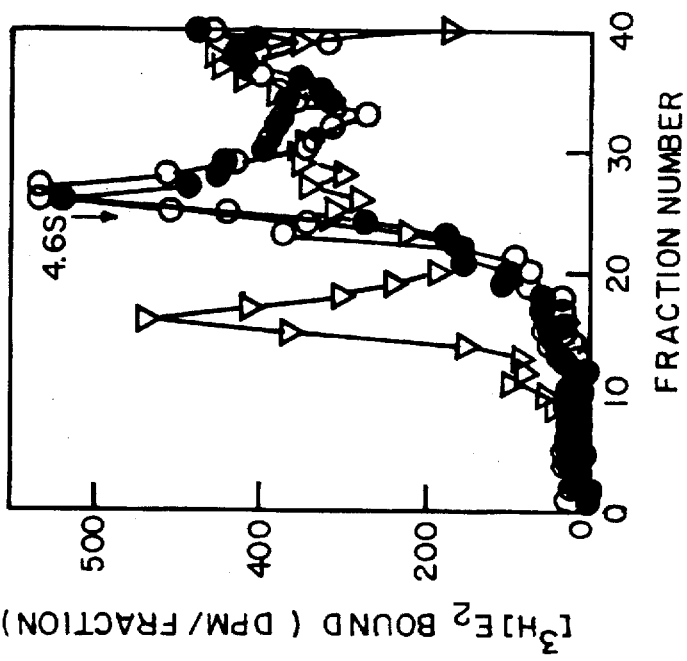

Detection Of An Altered A/B Region Of ER In Clinical Human Breast Cancer Specimens An analysis of ER from 29 human breast tumor clinical specimens was undertaken with monoclonal antibody #213 (an MAb directed to the ER DNA-binding C domain alone) and monoclonal antibody NMT-1C6 (directed specifically to the A/B region) demonstrated the presence of altered estrogen receptors in these tumors. Based on this analysis, the tumors were able to be classified into four groups (I–IV). In group I (10 tumor specimens), ER bound both the A/B domain and the C domain specifically site-directed antibodies, as demonstrated by density shift of the ER-antibody complexes shown by FIG. 16A. In group II (3 tumor specimens), while the ER DNA-binding domain remained intact, the A/B region subdomain was functionally altered, as shown by the density shift of ER with monoclonal antibody #213 (the C domain MAb), but not with the NMT-1C6 specific for the A/B domain, as illustrated by FIG. 16B. In group III (13 tumor specimens), however, the DNA-binding C domain appeared defective, while the A/B region subdomain remained intact, as determined by density shift of ER with NMT-1C6 antibody, but not with monoclonal antibody #213 —as shown by FIG. 16C. In group IV (3 tumor specimens), ER did not bind either of the two antibodies, showing that ER in these tumors is altered in both the DNA and the A/B subdomains. This last result is shown by FIG. 16D.

E. Conclusions And Summary

The experiments and empirical data presented herein unequivocally show that the functional status of the A/B region and the activation and transformation capability for the hER protein can be determined using the structural isoform differences existing among the native (8S), activated (4S) and transformed (5S) isoforms of hER. While the polyclonal antisera do not show any differences in binding specificity and are thus unable to discriminate structurally among the three isoforms, the anti-A/B region hER monoclonal antibodies do provide such a discriminatory capability. The relationship between structural state and functional status is based—not on the presence of absence of particular amino acid residues in sequence—but rather on the distinctive ability to identify and distinguish among the 8S, 4S, and 5S isoforms of hER having the same amino acids in sequence. Clearly, the monoclonal antibodies provide a proven capability to bind specifically with a single epitope within the A/B domain in the activated but untransformed (4S) form and in the activated and transformed (5S) form of hER; however, they do not bind with the native (8S) form of hER. Thus, the basis for evaluating and determining the functional status of the A/B domain of an hER sample under test, lies in the power to identify and discriminate among the three isoforms of hER.

What I claim is:

1. A monoclonal antibody specific for an epitope within amino acid residues 1–184 of an estrogen receptor protein, said monoclonal antibody having binding specificity for a single epitope within the A/B domains in the activated but untransformed (4S) forms and in the activated and transformed (5S) forms of estrogen receptor protein but which does not bind with native (8S) forms of estrogen receptor protein.

2. The monoclonal antibody as recited in claim 1 wherein said epitope lies within amino acid residues 140–154 of said A/B domains.

3. The monoclonal antibody as recited in claim 1 wherein said epitope lies within amino acid residues 155–169 of said A/B domains.

4. The monoclonal antibody as recited in claim 1 wherein said epitope lies within amino acid residues 170–184 of said A/B domains.

5. A hybridoma which produces a monoclonal antibody specific for an epitope within amino acid residues 1–184 of an estrogen receptor protein, said hybridoma comprising:

an antibody producing cell producing a monoclonal antibody having binding specificity for a single epitope within the A/B domains in the activated but untransformed (4S) forms and in the activated and transformed (5S) forms of estrogen receptor protein but which does not bind with native (8S) forms of estrogen receptor protein; and a tumor cell fused with said antibody producing cell.

6. The hybridoma as recited in claim 5 wherein said epitope lies within amino acid residues 140–154 of said A/B domains.

7. The hybridoma as recited in claim 5 wherein said epitope lies within amino acid residues 155–169 of said A/B domains.

8. The hybridoma as recited in claim 5 wherein said epitope lies within amino acid residues 170–184 of said A/B domains.

* * * * *